US006436410B1

(12) United States Patent
Krishnan et al.

(10) Patent No.: US 6,436,410 B1
(45) Date of Patent: Aug. 20, 2002

(54) DNA ENCODING NEOSPORA DIHYDROFOLATE REDUCTASE-THYMIDYLATE SYNTHASE

(75) Inventors: B. Rajendra Krishnan, East Lyme; S. Christine Yoder, Salem; Becky A. Durtschi, Ledyard, all of CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 09/203,895

(22) Filed: Dec. 2, 1998

Related U.S. Application Data

(60) Provisional application No. 60/067,507, filed on Dec. 4, 1997, and provisional application No. 60/095,213, filed on Aug. 3, 1998.

(51) Int. Cl.[7] .................... A61K 39/002; A61K 39/012; C07H 21/04; C07H 21/02; C12Q 1/68

(52) U.S. Cl. ............................... 424/265.1; 424/273.1; 424/191.1; 424/184.1; 424/200.1; 536/23.1; 536/23.7; 435/6; 435/91.4

(58) Field of Search ......................... 536/23.1; 435/325, 435/252.3, 254.11, 254.2, 183, 91.4, 6

(56) References Cited

U.S. PATENT DOCUMENTS

| | | | | |
|---|---|---|---|---|
| 5,643,718 A | | 7/1997 | Kim et al. | 435/6 |
| 5,707,617 A | | 1/1998 | Conrad et al. | 424/93.1 |
| 5,795,731 A | * | 8/1998 | Belfort et al. | |
| 5,849,564 A | * | 12/1998 | Chang et al. | |

FOREIGN PATENT DOCUMENTS

| | | |
|---|---|---|
| WO | 9525541 | 9/1995 |
| WO | 9717082 | 5/1997 |

OTHER PUBLICATIONS

Miyata et al : Br.J.Haematolgy., 88:156–165, 1994.*

Roos et al: J.Biol.Chem., 268 (9) :6269–80, 1993.*

Rudinger et al : peptide hormones, Univ.Park Press, 1976.*

Jenkins FJ : PCR Methods and applications, Cold Spring Harbor, 1994.*

Anneloor et al, 1990, Nature 348:174–175, "Targeted insertion of the neomycin phosphotransferase gene into the tubulin gene cluster of Trypanosoma brucei."

Barr et al., 1994, J. Vet. Diagn. Invest. 6:207–215, "Experimental reproduction of bovine fetal Neospora infection and death with a bovine Neospora isolate."

Cole et al., 1995, J. Parasitol. 81:730–732, "Vertical transmission of Neospora caninum in mice."

Conrad et al., 1993, Parasitol. 106:239–249, "In vitro isolation and characterization of a Neospora sp. from aborted bovine foetuses."

Cruz and Beverley, 1990, Nature 348:171–173, "Gene replacement in parasitic protozoa."

Donald and Roos, 1994, Mol. Biochem. Parasitol. 63:243–253, "Homologous recombination and gene replacement at the dihydrofolate reductase–thymidylate synthase locus in Toxoplasma gondii."

Dubey and Lindsay, 1993, Parasitol. Today 9:452–458 "Neosporosis."

Eid and Sollner–Webb, Proc. Natl. Acad. Sci. USA 88:2118–2121, "Stable integrative transformation of Trypanosoma brucei that occurs exclusively by homologous recombination."

Kim et al., 1993, Science 262:911–914, "Gene replacement in Toxoplasma gondii with chloramphenicol acetyltransferase as selectable marker."

LeBowitz et al., 1990, Proc. Natl. Acad. Sci. USA 87:9736–9740, "Development of a stable Leishmania expression vector and application to the study of parasite surface antigen genes."

Gwo–Shu et al., 1990, Science 250:1583–1586, "Homologous recombination and stable transformation in the parasitic protozoan Trypanosoma brucei."

Lindsay et al., 1995, Am. J. Vet. Res. 56:1176–1180, "Abortions, fetal deaths, and stillbirths in pregnant pygmy goats inoculated with tachyzoites of Neospora caninum."

Lindsay and Dubey, 1989, J. Parasitol. 75:722–779, "Neospora caninum (Protozoa: Apicomplexa) infections in mice."

Lindsay and Dubey, 1989, J. Parasitol. 75:163–165, "In vitro development of Neospora caninum (Protozoa: Apicomplexa) from dogs."

Lindsay and Dubey, 1990, J. Parasitol. 76:410–413, "Infections in mice with tachyzoites and bradyzoites of Neospora caninum (Protozoa: Apicomplexa)."

Marsh et al., 1995, J. Parasitol. 81:530–535, "Sequence analysis and comparison of ribosomal DNA from bovine Neospora to similar coccidial parasites."

Messina et al., 1995, Gene 165:213–217, "Stable DNA transformation of Toxoplasma gondii using phleomycin selection."

Sibley et al., 1994, Proc. Natl. Acad. Sci. USA 91:5508–5512, "Stable DNA transformation in the obligate intracellular parasite Toxoplasma gondii by complementation of tryptophan auxotrophy."

(List continued on next page.)

*Primary Examiner*—Mark Navarro
*Assistant Examiner*—Padmavathi Baskar
(74) *Attorney, Agent, or Firm*—Scully, Scott, Murphy & Presser

(57) ABSTRACT

The present invention provides isolated polynucleotide molecules comprising a nucleotide sequence encoding the DHFR-TS protein of Neospora which polynucleotide molecules are useful in preparing modified live vaccines against neosporosis, and as diagnostic reagents. The present invention further provides cloning and expression vectors, transformed host cells, substantially purified DHFR-TS proteins and peptide fragments, genetic constructs useful for targeted gene deletion, and vaccine compositions.

18 Claims, No Drawings

OTHER PUBLICATIONS

Soldati and Boothroyd, 1993, Science 260:349–352, "Transient transfection and expression in the obligate intracellular parasite Toxoplasma gondii."

Titus et al., 1995, Proc. Natl. Acad. Sci. USA 92:10267–10271–10271, "Development of a safe live Leishmania vaccine line by gene replacement."

Lindsay et al., 1996, Am. J. Vet. Res. 57(1):68–72, "Demonstration of synergistic effects of sulfonamides and dihydrofolate reductase/thymidylate synthase inhibitors against Neospora caninum tachyzoites in cultured cells, and characterization of mutants resistant to pyrimethamine."

Howe and Sibley, 1997, Methods: A Companion to Methods in Enzymology 13:123–133, "Development of Molecular Genetics of *Neospora caninum* : A complementary system to *Toxoplasma gondii* ".

* cited by examiner

SEQUENCE LISTING

```
<160> NUMBER OF SEQ ID NOS: 9

<210> SEQ ID NO 1
<211> LENGTH: 9603
<212> TYPE: DNA
<213> ORGANISM: Neospora caninum
<220> FEATURE:
<221> NAME/KEY: gene
<222> LOCATION: (2405)..(8199)

<400> SEQUENCE: 1
gcggccgccg gcacaatgcc gagggcagcg cagggaaaaa ccggtcgaag ctgcttcacg      60
tgtctgaaaa tagagccagc gctactgtcg cttcaaagaa cgagacttcc gcgccacaaa     120
tcggtagtga cggtggccgg aagcgaaaat tttacgacga gcagctgcca gtcggtgtgt     180
accgtcacca gcagaagtat gtcgcgaact gggtagatcc gaaaacccgg agacaaatca     240
aggtctgttt ccccatcgac gtgtgggag actctcaagc tcgcaacatg gctgccgttg      300
cgaggcgtga gcgctgcgtg gatgttgacg aggtggctgc tattttcaat cgtgaagagc     360
```

```
gcaccaagac atcaggacgt catccgagtc cttcgaggga tgacagcaaa cagacagcgt    420 cttcaatag tgctgttagg atgccagcag tccagggtgt ggattcaaaa acggagacgc    480
actcggctcc ggcgctcgaa agcgcgtaga gcctgaggcc acaccacttc tggttttcag    540
agagggcgtc gcactcacaa ttttttttcga cttctttccg cacactgggg ccgtgtgctc    600
gaacactttt tatccgtgtg accatgtgcc cgaacacttt ttatccgtgt gaccatgtgc    660
ccacgaacgc ggcgaggctt ccctgtgctc gtggatttta ttgagtgatt ttcttgtata    720
cagaaaacct gtttcgtttt gctgccagtc ttcacatacg cttgcaagca gagcgtgagt    780 aggggggggtt ccttgggaga gagcgcgaaa ggcgactttt tttatgacca gcgagagcgc    840
cgcagcagca caacgatcag aaaacacttg gacaaaattg gctctcgcca gggagaagtt    900
gataactaaa ctgcagtgga gaatccaaga tgcgaacgca gcctgcaaaa acatggcttc    960
agagctgcat gttcctttga tttaacgtgc acaccttgtc gtgcaaggtg ggcatcactg    1020
agggacttcg ccatcccgcg tactcgtcgc agcagtgcca cgcttctccg ggcgtccact    1080
gggccgaagt taatcgggc ggatcccaag ttaccgtcaa gtcccaaatc ttcagctgtt    1140
tgcaggaagg ttgctccgca cttgggtact gccgtgagaa gcagcggttc actgtgctgc    1200
gtcacctcgt ccacaggaac agacacactg gagctatgtc ggtggaccgg ctgcgtattc    1260
gatgaggttc agctgcggtc gttgcagagc tgcttttccc tcttgccaag acgatacgaa    1320
tagagtgtag cggaaggcac tgtacccaga agcattcagt tgcgctgttt cggatttcag    1380
tcgacacaga tctgttcgcg aacgacggcc ccgcagatct tgtgcccctg actcgggact    1440
cgtacagaag gcggttcgac gacgtttaga tgcgggcgac aagaattcgt gtcttaactt    1500
gctttcagcc tggtgtctac gtgccaaagt tcgctgaccg aaaagtcacc acggaagtgg    1560
attgctacgc agtcatatgc ccgatgccca ctccactgtg ctctttccgc agtgcttcgc    1620
cgccgaaaaa acgaggcgac tccggtttgc tccgtcctgc tccacaaaac tgaaggttcc    1680 tcagacccctt tagagactca aaacgcagcc tccaggacga ccgacgcgca gaagaaacca    1740
gcacgccact gctctctccg cctccagcgt gtctttgtgt ctcgtggcac ggcggtcggt    1800
ggttccgcct gcgtctcgcc tttttcgcgtt ccctgtctca gcgtgaacac catcactaca    1860
cccaccgcca gtgctagaac tggtccgaca ctctttcttc ctccaacgag cgcttcatta    1920
ggtcctttgt ttttcgacac tgcaaacttg cgtggttttt cacttcgcac gcggaagacc    1980
cgaacctgga ctgccgccgc ttgcacacta tagcggcctc gtctgccgtc tccgtcggag    2040 cctccccccct cgtcaacttt acggtccggt gccgcgaaag cgcatttggc gaatatatct    2100
ccggaaactc cacgctttt aaagccgtca ggctctcttc gttcttctcg tcgagctcgt    2160
tttctctgct tccttgactt gcttcgatct gcgcatcttc ctactcctcc ctggcccgtt    2220
aaacttcgag acaagggacg aggtgtgcac atctttcgct tgatacccaa ctctccccgg    2280
cttcgtgctg accgttttcc acttttacct cacggcaatg ccgagcgcgc ctctgagtgc    2340
ggctgggacg ggtgaagttg gaccgtctgt tgccgttcca actcgtggag ttgtgcagcg    2400
aaacatgcag aaaccagtgt ctcttattgc cgcgatgacc cccaggaggg gcatcggcgt    2460
caacaacggc ctgccatggc cccacttggc cacagatttc aaacacttt ctcgcgtgac    2520 gaaaacgacg gccgacgaag tctctcgcct gaacgcatgg cttccgaaaa aaattgccaa    2580
gacgggcgat tcgggacttc cctctcccgc cttcggtgtc aacagattca acgctgttgt    2640
catgggacga aaaacctggg agagcttgcc gctaaaattt cgtcccctcg tggaccggct    2700
```

-continued

```
gaatatcgtg gtttcctcct ccctgtaagc acacggcgca ggcgatgtgt ctgtgcgctc    2760
gcgacgtctc cgtgcgtgcc aagagactgg acgattccct ctgaaaagcc ttcgccggct    2820
ccattcctcg tagacgaacc acaaaccgcg agtgcgcttt cctcggagag aaaggccgca    2880
cgtctggatg caacacactg ggggactgc gatcgtatgt cctgataacc gaaatccgga     2940
aggctgactg aagacgcact ggcgttcgca aacatttctc catcgcttcg cgtggaccgg    3000
tgaacctgct ctctgcacaa ccagactcgt ggttcctacg ttgctgagca cggctgcata    3060 tatatata tatatatata tacatacgca tatgcgtata gaggttcccg cccgaagcgt      3120
gcttctgtcc gtcttccgtc cctgctgtcc tcccatcgcc atctccattt cctacgtgtc    3180
tttcgtcctt cccttgttca acggttgtca gcaaagaaga agacatcgcg gcggagaagc    3240
ctctagtcga aggccagcaa cgcgtgcgag tctgcgattc actccccgca gccctgcgcc    3300
ttgtggacga agagtacaga gagtctgttg accagattta tgttgtgggt aggtgtgcca    3360
agagcggcac agattcctct ctcgctcaga agtgcctggc aactgatctg cggcacgcgc    3420
cgcggatccc gatgcacatt gaggcttcgt gtacatactc cctgcgagct accagagggg    3480
ctgagaatct ccagataagc gtatatttct atgtgtttat gcatagatat ttagaacagg    3540
ctgaggagat gcggggaagg ctgacactga cggaatgcct tgccgcccac cagcagagga    3600
aggcggatgg ggacaacggc atgcagcctg ggacagcggc tgattcacgc cgacagcgca    3660 gccccgacg tcgtgaagc gtctcgaccg cctttttggg cgcgcctctc cgttccttct     3720
ttcgcccacg gcttcgtttc tctccattcc cactgcgtgt tggagcccgt ccgtccagtc    3780
tctctcagtt ctcttctttc ccttcagttg ctgtactctt ttcgccgtgc tccagttcct    3840
tgcgttgtgg ccttttccgc tcttcctatt ggcgtctcgc atccattgcg ttttctcggg    3900
tggtatccct ccgcctgcct tcaggaggag cggggctcta tgaggaagcc ctgtctctgg    3960
gcgtggtgtc tcacctctac atcacccgcg tggcgcgtga ctttccatgc gacgttttct    4020
ttcccgcttt ccccggagac tccattcttt caaacaagca ggcggcctcc gcgagtcagc    4080
cttcggctgc tgcggaaccg gtgtttgttc cgttttgccc ccagctcggg agagagaaga    4140
gcaatgaagc gtcgtaccga cccatcttta tttcaaagac ctactcggac aacggagtgc    4200
cctacgactt tgtggttctt gaaaaaggga ggaaggctga cgcttgcagc gccacggaat    4260
cggtaagtgg ctacggaggg gaaaagacga gagaaagagc gggcatccgg aacgagtgtc    4320
gcgaggcgac gttccatgcg tatccaagag agagggaaga gggaacacgc agcttgaggg    4380
gtaagctacg cgctcttttc ttttctccgt ggccgcggga gacgccgtaa agatggtgca    4440
aggacgcgca cgggcgtttc gccgttttcg gtttctgtcc actcttccag tgcgagcttc    4500
gcggcccttg gacctccacc ggagagacgt cgccagagac gaggcttccg tcttcctccg    4560
cctcagccgt tgcccaggtg ttggcttgga tggccgacga agaccggaaa aaatgcgaga    4620
agaaagaaat cattcgggca gtgcctcacg tccactttcg gggccacgaa gaattccagt    4680
acctcgacct cattgccgat attatcaaca acggagcgac aatggacgac cgaacgggta    4740
aacgcgacca cggaaaggca tcccgttcat gcggggctgt ctgctgagcc tcggttcctt    4800
cttccgcgct gtgcggcttt ccctgggggt ctttgcttct ctctgttcgc cgccttgcct    4860
gccacatttt cccttcattt tttttctctg tctcccttgc tcttttgtcc taacgttcgt    4920
actcgccttc gtctcgcagt ccacgcttca aaacagacgg gctaccgaaa cgtgttttcc    4980
ctctgcacgg ccttttttcac acgccgttgt cgcttgactc tcgctgacgc ggggtttgcc    5040
gcttcctgga agaaagaagg ccttttcctca tctgttcgcc cttttcgctg tttcacagaa    5100
```

```
agacgagaga gattccgtct ccattttctc aattcgcgtt tcgtgcccca agcagatgtg    5160
ccctgatctg gaggctcttc gccgctcccc ttctccctg tcgctgcttt caggcgttgg     5220
agtcatctcc aagttcggct gtaccatgcg gttctcgctg gataaggcct tccctctcct    5280
caccacaaag cgtgtgttct ggaaagggta cggcgccta cagaaatctg tatatattta     5340
acaggcacat gtgtgcgtgt ctgacctgca cacgtgttca taaacgtgca cgcaattgta    5400
tgtggctgcc gtggagtcgt ccacgaacag gaaatattca catgcatgca ctctacagac    5460
gtgcctggac tgcttctcta ccttcgtttg tctgtttatt tgctttaatt tcgcccggtg    5520
accgtcgcgc ctctgtctga ccgtgcattt gcttgcgtct catcgtagtg tgcgtatcga    5580
agacgagaga gcatgtgacg ctgttgtcta tgccgagtac gagaagtccg cacgacggtc    5640
gctgaacgat gttctttcc gtgtgggttg ctctcagagt cctcgaggag ctgttgtggt     5700
tcatccgcgg tgacacgaac gcgaatcacc tctctgaaaa gggcgtaaag gcaagtcttc    5760
aagcaccgct gctctcgttc aggctcctcc gcagacttgg cgctttcctt cgcggcgtca    5820
cccctccgag gcttcacgct tacattgagt gtacccgttt gtcttctaga ccgtctgctg    5880
cgtttgcagg ccccgcgtg agtgtaggcc cttcatcgtt gagtgtggcc gtagctttgc     5940
gcgacgaaga cagtcgatag gccttcaga gcacgttcct tctgtctccc gttttccccg     6000
ttttttcccg tgtcttcctc tgacagcctc gcacggctca catcccctct gagccgggac    6060
agggctcgcc taaggcagag taccacgctc cgtaacttcc ggcatgcgtt tctgggtttt    6120
cgttttagat ctgggacaag aatgtgacaa gagagttcct tgattcacgc aatctttccc    6180
accgagaggt cggagacatc ggcccgggtt acggcttcca gtggagacac ttcggcgcga    6240
cctacaagga catgcacacg gactacactg gtatgtcccg gcgttctttg aggggggaag    6300
ggaaagcagc cgaacccgcg aaacggcgct gatgcctgtt ctcgcttcgt gtgctggacc    6360
gaccgttcca gccatatcgc aggtttcaat agccgccaca aacggagatg aaaatgcaag    6420
gcgacgactc tgccgctcgcg cacaactggt gacagacgcc actccgtgtg gacgaattcg    6480
gttgcaaact gccaagcgat gaaagggccg tcgggtggta actccgtgcc cggcgcttg     6540 cacacaaata cccgtgtgtg tgtgtgtgtg cgtatgttga tgcaaagata cccctacgtg    6600
tgcatgtgta catacacgtg agaaattggt gcccgtcgtt gaaaaatgct cactcccatc    6660
cctcctggcg ttgcccattt gcaggtcagg gcgtagacca actgaagaag gtgatcaaca    6720
tgctgagaac gaatccaaca gaccggcgca tgctcatgac cgcttggaac cctgcgggtg    6780
agatctctgt cttcaatctc tccttccag ataatacgtg catttcaact ggaagctctt     6840
acacagccgt gtgcacaacg ggaagacgct gacacatacg tgttggtccc cccaacgtta    6900
tcttccgtgc cgtatctgtg tggctgctcc tctaaggtta ttgcgccgtg gtgatgtctc    6960
tcgtatctcg tctgtgctt tcgctggatg cctctgtgcc tagacatctc aaagtgtccc     7020
tcccgtgtgg ggtcccgcga aacacttgcc actggccttt tcgcctcttg ccgctgtcgt    7080
ctgttcctcg ggattcccta ctcggggacc tgccggtttc agtgcctttc ctccgcgggt    7140
gcttcttccc ccgtcctcgc gccttgtgtt tcttgccgt ggcgactgcg ccgccgtgca     7200
tgctgctcac ttcccccgt gcgcgtgtgt tttgtcctcg ccgtctctct ctttcccgtt     7260
cagcgctgga cgaaatggcg ttgccgcctt gccacttgct gtgtcagttc tacgtggaga    7320
acgacagaga cttgtcttgc gtcatgtatc agcggtcctg cgacgttggc ctcggggtgc    7380
cgttcaacat tgcgtcctat tcccttctga cgctcatggt tgcgcacgtc tgcaacctga    7440
```

-continued

```
agccgaagga gttcattcac ttcatgggca acacgcacgt ctactcgaac cacgtcgagg    7500
ccctgaagga gcagctgcgc agagaaccga gacctttccc catcgtgaac atcctgaaca    7560
aggaacgcat ccaggtgcga agcaactggg aaggaaacgg cacaacggac acgcaaacaa    7620
gcagaagagg cgaaacggac gacggcagcc gaggccccgg ccactgcgag ccgagcgcag    7680
acacgctgct tccagccggc ctatattcgg aaagaaaggg acagtgtcga agggagcaca    7740
cgagacgcaa caacgaaaag gaaacgcgat gcgtcgcaga tcggctcacc tatgtggtgc    7800
gcggtgcggc gcccagatgg cgcggctgca gcgctcgaag aagactgtc tttgggtgcg     7860 tgtgaacgtt tgtccctgac gcgcggctga cagaacatga gagggctttt ttctgtgttg    7920
cacgctctcc ggatgcatct ctttctgtgc cacgggaagc aaagacgtgt gtgttccccg    7980
ggaattcgga aaagacccga gcatccgctg ccggcgatgg ggggggaggg gccgggcatt    8040
ggatgcctcc cgcctcgtct tgtcgacggc cccaaaaccc gtcagtgcca cgttgtttgt    8100
gagtgtgttc gccaggaaat cgacgacttc accgccgagg atttcgaggt cgtgggctac    8160
gtgccgcatg gacgaatcca gatggagatg gctgtttagt ggaaaaatct gaaatatata    8220
tatatatata tatatatata tatatatagg ttcctggttt tgcaccgttt tttcttctcc    8280
ctccgaaggc attggtgaga gagcggtgga tgcgagggcg ctgaggccaa ttcagcggct    8340
gtttggtccc tcggggaagc aagaaacggg tttcgcttcg cctcgttgct ttccgaaaca    8400
accttaccgc gtttcaaagt cttttctctt tgtcaatgag cgccactact ttgtgggagt    8460
cacgaatgtg cgcgtatccg gccttgtatg gaggtgcggc tgccgcgctc gtcgccggaa    8520
cgctggactg tctgttgctt tcggggcctc tggcgtgctg cggcgtgggc ggggagtgg    8580 caggcgctac ccccccgtcg gtcctcggtg tgcttttgac tcttggcgag tgcgtgaaac    8640
ctaaatctcg acttgtttcg ctcgataagc tgcacactga gcactgaaga gttccccgca    8700
cattatgagg ccgcgcgctc tttcgcgcct ggcacacacg cctaacacag ggtagctgcc    8760
tgataaactg cctatcgcca ccaagggagc tgcctagcca agttgtcggt ggacaaaagt    8820
cctcacacgc cccgcagacc cggaagcaca cgtttcagag accaccggaa atgcatagtt    8880
cttcgtgccc tcgtcgttaa atacgtttcc tgtctcgtct gctggttttt gcttcgtgcg    8940
ttcgctcgcg ctaagatgtc tagaaacggt ggacgccgtt tgcggctctc tctgccgccc    9000
ttccgctgtg acttttccga cctgacctca cgcgcgtgtt ccacgtgaga caaccggtcg    9060
gcggccgagc aggagacttt gcgagaaagg aaacaagtcg gatgcacgaa cgtacgtaac    9120
cccgcctcca aagttccccg ctccaaagag gaacgcggcg aggcgactcc tccggcgttg    9180
cctacctcgc ctccacgcct aaagaggact gcagtgggtc gacgctcccg tccgcattgt    9240
aaaaaggggg aaacaagacg agattcacgt ggaagaacca gaaacaacac cgaagcgacg    9300
ctgtcaatcc ccacgggcgc gcagccttct cccgaccgca ctccgccgca tgcaagagcc    9360
ctcgagtgct ccccgcagc tggcctttcc ctgtcgcctt ggaagcagag tgaacacaaa     9420
gagcagagac tagccagggc gaggaagcct cagaaaaact gacggcgagg aacggcagtc    9480
cgccggaaac aggggaaggc agacggcgaa tccgccgccg aagagaggac aaaaagagaa    9540 gaaaaaggc aaccgcgtgc cgaaaactgg gtaacgggac gacaggcagg aggcataaag     9600
ctt                                                                 9603
```

<210> SEQ ID NO 2
<211> LENGTH: 1839
<212> TYPE: DNA
<213> ORGANISM: Neospora caninum

```
<220> FEATURE:
<221> NAME/KEY: CDS
<222> LOCATION: (1)..(1839)

<400> SEQUENCE: 2
```

| | | | | | | | | | | | | | | | | |
|---|---|---|---|---|---|---|---|---|---|---|---|---|---|---|---|---|
| atg | cag | aaa | cca | gtg | tct | ctt | att | gcc | gcg | atg | acc | ccc | agg | agg | ggc | 48 |
| Met | Gln | Lys | Pro | Val | Ser | Leu | Ile | Ala | Ala | Met | Thr | Pro | Arg | Arg | Gly | |
| 1 | | | | 5 | | | | | 10 | | | | | 15 | | |
| atc | ggc | gtc | aac | aac | ggc | ctg | cca | tgg | ccc | cac | ttg | gcc | aca | gat | ttc | 96 |
| Ile | Gly | Val | Asn | Asn | Gly | Leu | Pro | Trp | Pro | His | Leu | Ala | Thr | Asp | Phe | |
| | | | 20 | | | | | 25 | | | | | 30 | | | |
| aaa | cac | ttt | tct | cgc | gtg | acg | aaa | acg | acg | gcc | gac | gaa | gtc | tct | cgc | 144 |
| Lys | His | Phe | Ser | Arg | Val | Thr | Lys | Thr | Thr | Ala | Asp | Glu | Val | Ser | Arg | |
| | | | 35 | | | | | 40 | | | | | 45 | | | |
| ctg | aac | gca | tgg | ctt | ccg | aaa | aaa | att | gcc | aag | acg | ggc | gat | tcg | gga | 192 |
| Leu | Asn | Ala | Trp | Leu | Pro | Lys | Lys | Ile | Ala | Lys | Thr | Gly | Asp | Ser | Gly | |
| | 50 | | | | | 55 | | | | | 60 | | | | | |
| ctt | ccc | tct | ccc | gcc | ttc | ggt | gtc | aac | aga | ttc | aac | gct | gtt | gtc | atg | 240 |
| Leu | Pro | Ser | Pro | Ala | Phe | Gly | Val | Asn | Arg | Phe | Asn | Ala | Val | Val | Met | |
| 65 | | | | | 70 | | | | | 75 | | | | | 80 | |
| gga | cga | aaa | acc | tgg | gag | agc | ttg | ccg | cta | aaa | ttt | cgt | ccc | ctc | gtg | 288 |
| Gly | Arg | Lys | Thr | Trp | Glu | Ser | Leu | Pro | Leu | Lys | Phe | Arg | Pro | Leu | Val | |
| | | | | 85 | | | | | 90 | | | | | 95 | | |
| gac | cgg | ctg | aat | atc | gtg | gtt | tcc | tcc | tcc | ctc | aaa | gaa | gaa | gac | atc | 336 |
| Asp | Arg | Leu | Asn | Ile | Val | Val | Ser | Ser | Ser | Leu | Lys | Glu | Glu | Asp | Ile | |
| | | | 100 | | | | | 105 | | | | | 110 | | | |
| gcg | gcg | gag | aag | cct | cta | gtc | gaa | ggc | cag | caa | cgc | gtg | cga | gtc | tgc | 384 |
| Ala | Ala | Glu | Lys | Pro | Leu | Val | Glu | Gly | Gln | Gln | Arg | Val | Arg | Val | Cys | |
| | | | 115 | | | | | 120 | | | | | 125 | | | |
| gat | tca | ctc | ccc | gca | gcc | ctg | cgc | ctt | gtg | gac | gaa | gag | tac | aga | gag | 432 |
| Asp | Ser | Leu | Pro | Ala | Ala | Leu | Arg | Leu | Val | Asp | Glu | Glu | Tyr | Arg | Glu | |
| | 130 | | | | | 135 | | | | | 140 | | | | | |
| tct | gtt | gac | cag | att | tat | gtt | gtg | gga | gga | gcg | ggg | ctc | tat | gag | gaa | 480 |
| Ser | Val | Asp | Gln | Ile | Tyr | Val | Val | Gly | Gly | Ala | Gly | Leu | Tyr | Glu | Glu | |
| 145 | | | | | 150 | | | | | 155 | | | | | 160 | |
| gcc | ctg | tct | ctg | ggc | gtg | gtg | tct | cac | ctc | tac | atc | acc | cgc | gtg | gcg | 528 |
| Ala | Leu | Ser | Leu | Gly | Val | Val | Ser | His | Leu | Tyr | Ile | Thr | Arg | Val | Ala | |
| | | | | 165 | | | | | 170 | | | | | 175 | | |
| cgt | gac | ttt | cca | tgc | gac | gtt | ttc | ttt | ccc | gct | ttc | ccc | gga | gac | tcc | 576 |
| Arg | Asp | Phe | Pro | Cys | Asp | Val | Phe | Phe | Pro | Ala | Phe | Pro | Gly | Asp | Ser | |
| | | | 180 | | | | | 185 | | | | | 190 | | | |
| att | ctt | tca | aac | aag | cag | gcg | gcc | tcc | gcg | agt | cag | cct | tcg | gct | gct | 624 |
| Ile | Leu | Ser | Asn | Lys | Gln | Ala | Ala | Ser | Ala | Ser | Gln | Pro | Ser | Ala | Ala | |
| | | | 195 | | | | | 200 | | | | | 205 | | | |
| gcg | gaa | ccg | gtg | ttt | gtt | ccg | ttt | tgc | ccc | cag | ctc | ggg | aga | gag | aag | 672 |
| Ala | Glu | Pro | Val | Phe | Val | Pro | Phe | Cys | Pro | Gln | Leu | Gly | Arg | Glu | Lys | |
| | 210 | | | | | 215 | | | | | 220 | | | | | |
| agc | aat | gaa | gcg | tcg | tac | cga | ccc | atc | ttt | att | tca | aag | acc | tac | tcg | 720 |
| Ser | Asn | Glu | Ala | Ser | Tyr | Arg | Pro | Ile | Phe | Ile | Ser | Lys | Thr | Tyr | Ser | |
| 225 | | | | | 230 | | | | | 235 | | | | | 240 | |
| gac | aac | gga | gtg | ccc | tac | gac | ttt | gtg | gtt | ctt | gaa | aaa | ggg | agg | aag | 768 |
| Asp | Asn | Gly | Val | Pro | Tyr | Asp | Phe | Val | Val | Leu | Glu | Lys | Gly | Arg | Lys | |
| | | | | 245 | | | | | 250 | | | | | 255 | | |
| gct | gac | gct | tgc | agc | gcc | acg | gaa | tcg | tgc | gag | ctt | cgc | ggc | cct | tgg | 816 |
| Ala | Asp | Ala | Cys | Ser | Ala | Thr | Glu | Ser | Cys | Glu | Leu | Arg | Gly | Pro | Trp | |
| | | | 260 | | | | | 265 | | | | | 270 | | | |
| acc | tcc | acc | gga | gag | acg | tcg | cca | gag | acg | agg | ctt | ccg | tct | tcc | tcc | 864 |
| Thr | Ser | Thr | Gly | Glu | Thr | Ser | Pro | Glu | Thr | Arg | Leu | Pro | Ser | Ser | Ser | |
| | | | 275 | | | | | 280 | | | | | 285 | | | |
| gcc | tca | gcc | gtt | gcc | cag | gtg | ttg | gct | tgg | atg | gcc | gac | gaa | gac | cgg | 912 |

```
Ala Ser Ala Val Ala Gln Val Leu Ala Trp Met Ala Asp Glu Asp Arg
    290                 295                 300 aaa aaa tgc gag aag aaa gaa atc att cgg gca gtg cct cac gtc cac        960
Lys Lys Cys Glu Lys Lys Glu Ile Ile Arg Ala Val Pro His Val His
305                 310                 315                 320 ttt cgg ggc cac gaa gaa ttc cag tac ctc gac ctc att gcc gat att       1008
Phe Arg Gly His Glu Glu Phe Gln Tyr Leu Asp Leu Ile Ala Asp Ile
                325                 330                 335 atc aac aac gga gcg aca atg gac gac cga acg ggc gtt gga gtc atc       1056
Ile Asn Asn Gly Ala Thr Met Asp Asp Arg Thr Gly Val Gly Val Ile
        340                 345                 350 tcc aag ttc ggc tgt acc atg cgg ttc tcg ctg gat aag gcc ttc cct       1104
Ser Lys Phe Gly Cys Thr Met Arg Phe Ser Leu Asp Lys Ala Phe Pro
            355                 360                 365 ctc ctc acc aca aag cgt gtg ttc tgg aaa gga gtc ctc gag gag ctg       1152
Leu Leu Thr Thr Lys Arg Val Phe Trp Lys Gly Val Leu Glu Glu Leu
370                 375                 380 ttg tgg ttc atc cgc ggt gac acg aac gcg aat cac ctc tct gaa aag       1200
Leu Trp Phe Ile Arg Gly Asp Thr Asn Ala Asn His Leu Ser Glu Lys
385                 390                 395                 400 ggc gta aag atc tgg gac aag aat gtg aca aga gag ttc ctt gat tca       1248
Gly Val Lys Ile Trp Asp Lys Asn Val Thr Arg Glu Phe Leu Asp Ser
                405                 410                 415 cgc aat ctt tcc cac cga gag gtc gga gac atc ggc ccg ggt tac ggc       1296
Arg Asn Leu Ser His Arg Glu Val Gly Asp Ile Gly Pro Gly Tyr Gly
        420                 425                 430 ttc cag tgg aga cac ttc ggc gcg acc tac aag gac atg cac acg gac       1344
Phe Gln Trp Arg His Phe Gly Ala Thr Tyr Lys Asp Met His Thr Asp
            435                 440                 445 tac act ggt cag ggc gta gac caa ctg aag aag gtg atc aac atg ctg       1392
Tyr Thr Gly Gln Gly Val Asp Gln Leu Lys Lys Val Ile Asn Met Leu
450                 455                 460 aga acg aat cca aca gac cgg cgc atg ctc atg acc gct tgg aac cct       1440
Arg Thr Asn Pro Thr Asp Arg Arg Met Leu Met Thr Ala Trp Asn Pro
465                 470                 475                 480 gcg gcg ctg gac gaa atg gcg ttg ccg cct tgc cac ttg ctg tgt cag       1488
Ala Ala Leu Asp Glu Met Ala Leu Pro Pro Cys His Leu Leu Cys Gln
                485                 490                 495 ttc tac gtg gag aac gac aga gac ttg tct tgc gtc atg tat cag cgg       1536
Phe Tyr Val Glu Asn Asp Arg Asp Leu Ser Cys Val Met Tyr Gln Arg
        500                 505                 510 tcc tgc gac gtt ggc ctc ggg gtg ccg ttc aac att gcg tcc tat tcc       1584
Ser Cys Asp Val Gly Leu Gly Val Pro Phe Asn Ile Ala Ser Tyr Ser
            515                 520                 525 ctt ctg acg ctc atg gtt gcg cac gtc tgc aac ctg aag ccg aag gag       1632
Leu Leu Thr Leu Met Val Ala His Val Cys Asn Leu Lys Pro Lys Glu
530                 535                 540 ttc att cac ttc atg ggc aac acg cac gtc tac tcg aac cac gtc gag       1680
Phe Ile His Phe Met Gly Asn Thr His Val Tyr Ser Asn His Val Glu
545                 550                 555                 560 gcc ctg aag gag cag ctg cgc aga gaa ccg aga cct ttc ccc atc gtg       1728
Ala Leu Lys Glu Gln Leu Arg Arg Glu Pro Arg Pro Phe Pro Ile Val
                565                 570                 575 aac atc ctg aac aag gaa cgc atc cag gaa atc gac gac ttc acc gcc       1776
Asn Ile Leu Asn Lys Glu Arg Ile Gln Glu Ile Asp Asp Phe Thr Ala
        580                 585                 590 gag gat ttc gag gtc gtg ggc tac gtg ccg cat gga cga atc cag atg       1824
Glu Asp Phe Glu Val Val Gly Tyr Val Pro His Gly Arg Ile Gln Met
            595                 600                 605
```

```
gag atg gct gtt tag                                          1839
Glu Met Ala Val
    610
```

<210> SEQ ID NO 3
<211> LENGTH: 612
<212> TYPE: PRT
<213> ORGANISM: Neospora caninum

<400> SEQUENCE: 3

```
Met Gln Lys Pro Val Ser Leu Ile Ala Met Thr Pro Arg Arg Gly
 1               5                  10                  15

Ile Gly Val Asn Asn Gly Leu Pro Trp Pro His Leu Ala Thr Asp Phe
                 20                  25                  30

Lys His Phe Ser Arg Val Thr Lys Thr Thr Ala Asp Glu Val Ser Arg
             35                  40                  45

Leu Asn Ala Trp Leu Pro Lys Lys Ile Ala Lys Thr Gly Asp Ser Gly
         50                  55                  60

Leu Pro Ser Pro Ala Phe Gly Val Asn Arg Phe Asn Ala Val Val Met
 65                  70                  75                  80

Gly Arg Lys Thr Trp Glu Ser Leu Pro Leu Lys Phe Arg Pro Leu Val
                 85                  90                  95

Asp Arg Leu Asn Ile Val Val Ser Ser Leu Lys Glu Glu Asp Ile
                100                 105                 110

Ala Ala Glu Lys Pro Leu Val Glu Gly Gln Gln Arg Val Arg Val Cys
            115                 120                 125

Asp Ser Leu Pro Ala Ala Leu Arg Leu Val Asp Glu Glu Tyr Arg Glu
        130                 135                 140

Ser Val Asp Gln Ile Tyr Val Val Gly Gly Ala Gly Leu Tyr Glu Glu
145                 150                 155                 160

Ala Leu Ser Leu Gly Val Val Ser His Leu Tyr Ile Thr Arg Val Ala
                165                 170                 175

Arg Asp Phe Pro Cys Asp Val Phe Phe Pro Ala Phe Pro Gly Asp Ser
            180                 185                 190

Ile Leu Ser Asn Lys Gln Ala Ala Ser Ala Ser Gln Pro Ser Ala Ala
        195                 200                 205

Ala Glu Pro Val Phe Val Pro Phe Cys Pro Gln Leu Gly Arg Glu Lys
    210                 215                 220

Ser Asn Glu Ala Ser Tyr Arg Pro Ile Phe Ile Ser Lys Thr Tyr Ser
225                 230                 235                 240

Asp Asn Gly Val Pro Tyr Asp Phe Val Val Leu Glu Lys Gly Arg Lys
                245                 250                 255

Ala Asp Ala Cys Ser Ala Thr Glu Ser Cys Glu Leu Arg Gly Pro Trp
            260                 265                 270

Thr Ser Thr Gly Glu Thr Ser Pro Glu Thr Arg Leu Pro Ser Ser Ser
        275                 280                 285

Ala Ser Ala Val Ala Gln Val Leu Ala Trp Met Ala Asp Glu Asp Arg
    290                 295                 300

Lys Lys Cys Glu Lys Lys Glu Ile Ile Arg Ala Val Pro His Val His
305                 310                 315                 320

Phe Arg Gly His Glu Glu Phe Gln Tyr Leu Asp Leu Ile Ala Asp Ile
                325                 330                 335

Ile Asn Asn Gly Ala Thr Met Asp Asp Arg Thr Gly Val Gly Val Ile
            340                 345                 350

Ser Lys Phe Gly Cys Thr Met Arg Phe Ser Leu Asp Lys Ala Phe Pro
```

-continued

```
            355                 360                 365
Leu Leu Thr Thr Lys Arg Val Phe Trp Lys Gly Val Leu Glu Glu Leu
    370                 375                 380

Leu Trp Phe Ile Arg Gly Asp Thr Asn Ala Asn His Leu Ser Glu Lys
385                 390                 395                 400

Gly Val Lys Ile Trp Asp Lys Asn Val Thr Arg Glu Phe Leu Asp Ser
                405                 410                 415

Arg Asn Leu Ser His Arg Glu Val Gly Asp Ile Gly Pro Gly Tyr Gly
                420                 425                 430

Phe Gln Trp Arg His Phe Gly Ala Thr Tyr Lys Asp Met His Thr Asp
                435                 440                 445

Tyr Thr Gly Gln Gly Val Asp Gln Leu Lys Lys Val Ile Asn Met Leu
    450                 455                 460

Arg Thr Asn Pro Thr Asp Arg Arg Met Leu Met Thr Ala Trp Asn Pro
465                 470                 475                 480

Ala Ala Leu Asp Glu Met Ala Leu Pro Pro Cys His Leu Leu Cys Gln
                485                 490                 495

Phe Tyr Val Glu Asn Asp Arg Asp Leu Ser Cys Val Met Tyr Gln Arg
                500                 505                 510

Ser Cys Asp Val Gly Leu Gly Val Pro Phe Asn Ile Ala Ser Tyr Ser
                515                 520                 525

Leu Leu Thr Leu Met Val Ala His Val Cys Asn Leu Lys Pro Lys Glu
    530                 535                 540

Phe Ile His Phe Met Gly Asn Thr His Val Tyr Ser Asn His Val Glu
545                 550                 555                 560

Ala Leu Lys Glu Gln Leu Arg Arg Glu Pro Arg Pro Phe Pro Ile Val
                565                 570                 575

Asn Ile Leu Asn Lys Glu Arg Ile Gln Glu Ile Asp Asp Phe Thr Ala
                580                 585                 590

Glu Asp Phe Glu Val Val Gly Tyr Val Pro His Gly Arg Ile Gln Met
        595                 600                 605

Glu Met Ala Val
    610

<210> SEQ ID NO 4
<211> LENGTH: 20
<212> TYPE: DNA
<213> ORGANISM: Neospora caninum

<400> SEQUENCE: 4
atgcagaaac cggtgtgtct                                                 20

<210> SEQ ID NO 5
<211> LENGTH: 20
<212> TYPE: DNA
<213> ORGANISM: Neospora caninum

<400> SEQUENCE: 5
agggaagagg aaacgacgat                                                 20

<210> SEQ ID NO 6
<211> LENGTH: 22
<212> TYPE: DNA
<213> ORGANISM: Neospora caninum

<400> SEQUENCE: 6
cccctcgtgg accggctgaa ta                                              22
```

```
<210> SEQ ID NO 7
<211> LENGTH: 21
<212> TYPE: DNA
<213> ORGANISM: Neospora caninum

<400> SEQUENCE: 7
tccgtgcgtg ccaagagact g                                               21

<210> SEQ ID NO 8
<211> LENGTH: 22
<212> TYPE: DNA
<213> ORGANISM: Neospora caninum

<400> SEQUENCE: 8
atggagatgg cgatgggagg ac                                              22

<210> SEQ ID NO 9
<211> LENGTH: 22
<212> TYPE: DNA
<213> ORGANISM: Neospora caninum

<400> SEQUENCE: 9
agtatgtaca cgaagcctca at                                              22
```

US 6,436,410 B1

DNA ENCODING NEOSPORA DIHYDROFOLATE REDUCTASE-THYMIDYLATE SYNTHASE

This application claims priority under 35 U.S.C. §119(e) from U.S. provisional application Ser. No. 60/067,507, filed Dec. 4, 1997, and U.S. provisional application Ser. No. 60/095,213, filed Aug. 3, 1998.

1. FIELD OF THE INVENTION

The present invention is in the field of animal health, and is directed to vaccine compositions and diagnostics for disease. More particularly, the present invention relates to polynucleotide molecules comprising a nucleotide sequence encoding the dihydrofolate reductase-thymidylate synthase (DHFR-TS) protein of Neospora, which polynucleotide molecules are useful in the production of vaccines against neosporosis, and as diagnostic reagents.

2. BACKGROUND OF THE INVENTION

Neospora is a pathogenic protozoan parasite of animals that has been recognized as a major cause of abortion, neonatal death, congenital infection, and encephalitic disease in mammals. Dubey and Lindsay, 1996, Vet. Parasitol. 67:1–59; Dubey and Lindsay, 1993, Parasitology Today, 9:452458. *N. caninum* infects dogs, and congenitally infects pups, often leading to paralysis. Tachyzoites of *N. caninum* have been isolated from naturally infected pups. Lindsay and Dubey, 1989, J. Parasitol. 75:163–165. Neospora is a major cause of abortion in dairy cattle. Cases of Neospora-related disease, i.e., neosporosis, have also been reported in goats, sheep and horses.

Although *N. caninum* is superficially similar to the pathogen, *Toxoplasma gondii*, *N. caninum* and *T. gondii* have been distinguished from each other both antigenically and ultrastructurally. Dubey and Lindsay, 1993, above. In addition, Neospora-like protozoan parasites isolated from the brains of aborted bovine fetuses and continuously cultured in vitro were shown to be antigenically and ultrastructurally distinct from both *T. gondii* and *Hammondia hammondi*, and were most similar to *N. caninum*. Conrad et al., 1993, Parasitology 106:239–249. Furthermore, analysis of nuclear small subunit ribosomal RNA genes revealed no nucleotide differences between strains of Neospora isolated from cattle and dogs, but showed consistent differences between Neospora and *T. gondii*. Marsh et al., 1995, J. Parasitol. 81:530–535.

The etiologic role of a bovine isolate of Neospora in bovine abortion and congenital disease has been confirmed. Barr et al., 1994, J. Vet. Diag. Invest. 6:207–215. A rodent model of central nervous system neosporosis has been developed using inbred BALB/c mice infected with *N. caninum*. Lindsay et al., 1995, J. Parasitol. 81:313–315. In addition, models to study transplacental transmission of *N. caninum* in pregnant outbred and inbred mice have been described by Cole et al., 1995, J. Parasitol. 81:730–732, and by Long et al., 1996, J. Parasitol. 82:608–611, respectively. Furthermore, an experimental *N. caninum* pygmy goat model that closely resembles naturally acquired Neospora-induced cattle abortion has been demonstrated. Lindsay et al., 1995, Am. J. Vet. Res. 56:1176–1180.

In protozoans such as *T. gondii* and Neospora, the essential metabolic enzymes dihydrofolate reductase (DHFR) and thymidylate synthase (TS) are known to reside on the same protein molecule in two distinct enzymatic domains, i.e., the "DHFR domain" and the "TS domain." In *T. gondii*, the DHFR and TS domains are reported to be separated by a junctional region of ~70 amino acids. Roos, 1993, J. Biol. Chem. 268:6269–6280. This bifunctional protein has served in at least one parasitic species as a target for deletion to create an attenuated strain for use in a live vaccine. Thus, Titus et al., 1995, Proc. Natl. Acad. Sci. 92:10267–10271 describes the targeted deletion by homologous recombination of the DHFR-TS gene from the protozoan parasite Leishmania major to produce dhfr⁻-ts⁻ null mutant cells for use in a vaccine against a virulent strain of *L. major*.

3. SUMMARY OF THE INVENTION

The present invention provides an isolated polynucleotide molecule comprising a nucleotide sequence that encodes a Neospora DHFR-TS protein. In a preferred embodiment, the Neospora DHFR-TS protein comprises the amino acid sequence of SEQ ID NO:3 or the amino acid sequence of a DHFR-TS protein as encoded by the DHFR-TS gene as present in phage λNclDHFRTS (ATCC Accession No. 209512). In a non-limiting embodiment, the isolated polynucleotide molecule comprises the nucleotide sequence of the Neospora DHFR-TS gene. In a preferred embodiment, the isolated polynucleotide molecule comprising the nucleotide sequence of the Neospora DHFR-TS gene comprises the nucleotide sequence of SEQ ID NO:1 from about nt 2405 to about nt 8199, or a nucleotide sequence that is the same as the nucleotide sequence of the DHFR-TS gene as present in phage λNclDHFRTS (ATCC Accession No. 209512). In a further non-limiting embodiment, the polynucleotide molecule encoding the DHFR-TS protein comprises the nucleotide sequence of SEQ ID NO:2.

The present invention further provides an isolated polynucleotide molecule that is substantially homologous to a polynucleotide molecule comprising the nucleotide sequence of the DHFR-TS gene as shown in SEQ ID NO:1 from about nt 2405 to about nt 8199, or the nucleotide sequence of the DHFR-TS gene as present in phage λNclDHFRTS (ATCC Accession No. 209512), or the nucleotide sequence of SEQ ID NO:2.

The present invention further provides an isolated polynucleotide molecule comprising a nucleotide sequence that encodes a polypeptide that is substantially homologous to a Neospora DHFR-TS protein having the amino acid sequence of SEQ ID NO:3, or the amino acid sequence of a DHFR-TS protein as encoded by the DHFR-TS gene as present in phage λNclDHFRTS (ATCC Accession No. 209512).

The present invention further provides a polynucleotide molecule consisting of a nucleotide sequence that is a substantial portion of any of the aforementioned polynucleotide molecules. In a preferred embodiment, the polynucleotide molecule consists of a nucleotide sequence that encodes a peptide fragment of any of the aforementioned Neospora DHFR-TS proteins or substantially homologous polypeptides, such as a polypeptide consisting of the DHFR domain or the TS domain of the DHFR-TS protein.

In addition to the nucleotide sequences of any of the aforementioned DHFR-TS-related polynucleotide molecules, polynucleotide molecules of the present invention can further comprise, or alternatively may consist of, nucleotide sequences that naturally flank the DHFR-TS gene in situ in *N. caninum*, such as, e.g., the flanking nucleotide sequences shown in SEQ ID NO:1, or portions thereof.

The present invention further provides compositions and methods for the cloning and expression of a polynucleotide molecule of the present invention, including cloning vectors, expression vectors, and transformed host cells comprising said vectors. In a non-limiting embodiment, the present invention provides a cloning vector comprising a polynucleotide molecule having the nucleotide sequence of the DHFR-TS gene of *N. caninum* strain NC-1, such as, e.g., a λ phage cloning vector designated as λNclDHFRTS (ATCC Accession No. 209512).

The present invention further provides a partially or substantially purified protein comprising the amino acid sequence of the Neospora DHFR-TS protein. In a non-limiting embodiment, the protein comprises the amino acid sequence of SEQ ID NO:3, or an amino acid sequence of a DHFR-TS protein as encoded by the DHFR-TS gene present in phage λNclDHFRTS (ATCC Accession No. 209512). The present invention further provides polypeptides that are substantially homologous to a Neospora DHFR-TS protein. The present invention further provides peptide fragments of any of the aforementioned proteins or polypeptides, such as, e.g., a polypeptide consisting of an isolated Neospora DHFR or TS domain.

The present invention further provides antibodies raised against a Neospora DHFR-TS protein or against a peptide fragment of said protein.

The present invention further provides genetic constructs comprising any of the aforementioned polynucleotide molecules such as, e.g., a polynucleotide molecule comprising the nucleotide sequence of the DHFR-TS gene, as shown in SEQ ID NO:1 from about nt 2405 to about nt 8199, or as present in phage λNclDHFRTS (ATCC Accession No. 209512), or a polynucleotide molecule consisting of nucleotide sequence which is a substantial portion of any of said nucleotide sequences, but modified by having one or more nucleotide deletions, insertions and/or substitutions therein, or consisting of one or more nucleotide sequences that naturally flank the DHFR-TS gene in situ in *N. caninum*; such that the polynucleotide molecule, when inserted into, or used to replace a portion of, a wild-type DHFR-TS gene, results in a modified DHFR-TS gene sequence that encodes a partially defective or fully defective protein, or fails to encode or produce any protein at all. Such genetic constructs are useful in producing modified Neospora cells in which the DHFR-TS gene or a portion thereof has been partially or completely disabled, thereby resulting in cells exhibiting either a dhfr$^-$, or a ts$^-$, or a dhfr$^-$-ts$^-$ mutant phenotype (hereinafter referred to collectively as a dhfr$^-$-ts$^-$ phenotype).

The present invention further provides modified live Neospora cells in which the native DHFR-TS gene, or a portion thereof, has been partially or completely disabled. In a preferred embodiment, the Neospora cells exhibit a dhfr$^-$-ts$^-$ mutant phenotype as a result of disruption of the DHFR-TS gene through homologous recombination with a genetic construct of the invention. Such modified live Neospora cells are useful in vaccine compositions to protect mammals against neosporosis. The present invention further provides a method of preparing the modified live Neospora cells.

The present invention further provides a vaccine against neosporosis, comprising an immunologically effective amount of the modified live Neospora cells of the present invention, and a veterinarily acceptable carrier. The present invention further provides a combination vaccine for protecting a mammal against neosporosis and, optionally, one or more other diseases or pathological conditions that can afflict the mammal, which combination vaccine comprises an immunologically effective amount of a first component comprising modified live Neospora cells of the present invention; an immunologically effective amount of a second component capable of inducing a protective response against a disease or pathological condition that can afflict the mammal; and a veterinarily acceptable carrier. The present invention further provides a method of preparing the vaccine of the present invention, comprising combining an immunologically effective amount of the modified live Neospora cells of the present invention with a veterinarily acceptable carrier. The present invention further provides a method of vaccinating a mammal against neosporosis, comprising administering to the mammal the vaccine of the present invention.

The present invention further provides a kit for vaccinating a mammal against neosporosis, comprising a first container having a composition comprising an immunologically effective amount of modified live Neospora cells of the present invention, and a second container having a veterinarily acceptable carrier or diluent.

4. DETAILED DESCRIPTION OF THE INVENTION

4.1. Polynucleotide Molecules Encoding Neospora DHFR-TS

The present invention provides: (i) an isolated polynucleotide molecule comprising a nucleotide sequence encoding a Neospora DHFR-TS protein, including an isolated polynucleotide molecule comprising the nucleotide sequence of the Neospora DHFR-TS gene; (ii) an isolated polynucleotide molecule that is substantially homologous to any of the aforementioned polynucleotide molecules; (iii) an isolated polynucleotide molecule comprising a nucleotide sequence that encodes a polypeptide that is substantially homologous to a Neospora DHFR-TS protein; and (iv) a polynucleotide molecule consisting of nucleotide sequence that is a substantial portion of any of the aforementioned polynucleotide molecules, including a polynucleotide molecule consisting of nucleotide sequence that encodes a peptide fragment of any of the aforementioned Neospora DHFR-TS proteins or substantially homologous polypeptides.

As used herein, the terms "gene," "polynucleotide molecule," "nucleotide sequence," "coding sequence," and "coding region" are intended to include both DNA and RNA molecules that can either be single-stranded or double-stranded. Also as used herein, the terms "gene," "coding sequence," and "coding region" are intended to refer to polynucleotide molecules that can be transcribed and translated (DNA), or translated (RNA), into a Neospora DHFR-TS protein, or into a polypeptide that is substantially homologous to a Neospora DHFR-TS protein, or into a peptide fragment of the aforementioned Neospora DHFR-TS protein or substantially homologous polypeptide, in a host cell expression system when placed in operative association with appropriate regulatory elements. The polynucleotide molecules can include, but are not limited to, one or more prokaryotic sequences, eukaryotic sequences, cDNA sequences, genomic DNA sequences (exons or introns), and chemically synthesized DNA and RNA sequences, or any combination thereof.

An isolated polynucleotide molecule of the present invention can have a nucleotide sequence from any species or strain of Neospora, but is preferably from a pathogenic species of Neospora such as *N. caninum*. A non-limiting example of a strain of *N. caninum* from which the polynucleotide molecule of the present invention can be isolated or derived is strain NC-1, which is available in host MARC-145 monkey kidney cells under Accession No. CRL-12231 from the American Type Culture Collection (ATCC), located at 12301 Parklawn Drive, Rockville, Md. 20852, USA. Strain NC-1 is also described in Dubey et al., 1988, J. Am. Vet. Med. Assoc. 193:1259–63, which publication is incorporated herein by reference. Alternatively, pathogenic strains or species of Neospora for use in practicing the present invention can be isolated from organs, tissues or body fluids of infected animals using standard isolation techniques such as those described in the publications reviewed above.

The present invention provides an isolated polynucleotide molecule comprising a nucleotide sequence that encodes a Neospora DHFR-TS protein. In a preferred embodiment, the Neospora DHFR-TS protein comprises the amino acid sequence of SEQ ID NO:3 or the amino acid sequence of a DHFR-TS protein as encoded by the DHFR-TS gene as present in phage λNclDHFRTS (ATCC Accession No. 209512). In a non-limiting embodiment, the isolated polynucleotide molecule comprises the nucleotide sequence of the Neospora DHFR-TS gene. In a preferred embodiment, the isolated polynucleotide molecule comprises the nucleotide sequence of the DHFR-TS gene of N. caninum strain NC-1 which comprises the nucleotide sequence of SEQ ID NO:1 from about nt 2405 to about nt 8199, or a nucleotide sequence that is the same as the nucleotide sequence of the DHFR-TS gene as present in phage λNclDHFRTS (ATCC Accession No. 209512). In SEQ ID NO:1, the predicted DHFR domain of the DHFR-TS gene is encoded from about nt 2405 to about nt 4664; the predicted TS domain of the DHFR-TS gene is encoded from about nt 4665 to about nt 8199. In a further non-limiting embodiment, the polynucleotide molecule encoding the DHFR-TS protein comprises the nucleotide sequence of SEQ ID NO:2, where the predicted DHFR domain is encoded by about nt 1 to about nt 969, and the predicted TS domain is encoded by about nt 970 to about nt 1836.

The present invention further provides an isolated polynucleotide molecule that is substantially homologous to a polynucleotide molecule comprising the nucleotide sequence of the DHFR-TS gene as shown in SEQ ID NO:1 from about nt 2405 to about nt 8199, or the nucleotide sequence of the DHFR-TS gene as present in phage λNclDHFRTS (ATCC Accession No. 209512), or the nucleotide sequence of SEQ ID NO:2. The term "substantially homologous" when used to refer to a DHFR-TS-related polynucleotide molecule means a polynucleotide molecule having a nucleotide sequence: (a) that encodes the same protein as the nucleotide sequence of the DHFR-TS gene shown in SEQ ID NO:1 from about nt 2405 to about nt 8199, or as present in phage λNclDHFRTS (ATCC Accession No. 209512), or the nucleotide sequence of SEQ ID NO:2, but that includes one or more silent changes to the nucleotide sequence according to the degeneracy of the genetic code; or (b) that hybridizes to the complement of a polynucleotide molecule having a nucleotide sequence that encodes the same protein as the nucleotide sequence of the DHFR-TS gene shown in SEQ ID NO:1 from about nt 2405 to about nt 8199, or as present in phage λNclDHFRTS (ATCC Accession No. 209512), or the nucleotide sequence of SEQ ID NO:2, under moderately stringent conditions, i.e., hybridization to filter-bound DNA in 0.5 M NaHPO$_4$, 7% sodium dodecyl sulfate (SDS), 1 mM EDTA at 65° C., and washing in 0.2×SSC/0.1% SDS at 42° C. (see Ausubel et al., (eds.), 1989, Current Protocols in Molecular Biology, Vol. I, Green Publishing Associates, Inc., and John Wiley & Sons, Inc., New York, at p. 2.10.3), and that is useful in practicing the present invention. In a preferred embodiment, the substantially homologous polynucleotide molecule hybridizes to the complement of a polynucleotide molecule having a nucleotide sequence that encodes the same protein as the nucleotide sequence of the DHFR-TS gene shown in SEQ ID NO:1 from about nt 2405 to about nt 8199, or as present in phage λNclDHFRTS (ATCC Accession No. 209512), or the nucleotide sequence of SEQ ID NO:2, under highly stringent conditions, i.e., hybridization to filter-bound DNA in 0.5 M NaHPO$_4$, 7% SDS, 1 mM EDTA at 65° C., and washing in 0.1×SSC/0.1% SDS at 68° C. (Ausubel et al., 1989, above), and is useful in practicing the present invention.

As used herein, a polynucleotide molecule is "useful in practicing the present invention" where the polynucleotide molecule can be used as a diagnostic reagent to detect the presence of a Neospora-specific polynucleotide in a fluid or tissue sample from a Neospora-infected animal, or where the polynucleotide molecule can be used to prepare a genetic construct useful in the preparation of modified live Neospora cells of the present invention, as described below in Section 4.4.

Substantially homologous polynucleotide molecules of the present invention do not include polynucleotide molecules having a nucleotide sequence encoding a DHFR-TS protein from T. gondii.

The present invention further provides an isolated polynucleotide molecule comprising a nucleotide sequence that encodes a polypeptide that is substantially homologous to a Neospora DHFR-TS protein having the amino acid sequence of SEQ ID NO:3, or the amino acid sequence of a DHFR-TS protein as encoded by the DHFR-TS gene as present in phage λNclDHFRTS (ATCC Accession No. 209512). As used herein to refer to polypeptides, the term "substantially homologous" refers to a polypeptide having an amino acid sequence: (a) that is preferably at least about 70%, more preferably at least about 80%, and most preferably at least about 90% the same as that of a DHFR-TS protein having the amino acid sequence of SEQ ID NO:3, or the amino acid sequence of a DHFR-TS protein as encoded by the DHFR-TS gene as present in phage λNclDHFRTS (ATCC Accession No. 209512), and which substantially homologous polypeptide is useful in practicing the present invention; and/or (b) in which one or more amino acid residues present in a Neospora DHFR-TS protein having the amino acid sequence of SEQ ID NO:3, or the amino acid sequence of a DHFR-TS protein as encoded by the DHFR-TS gene as present in phage λNclDHFRTS (ATCC Accession No. 209512), has been conservatively substituted with a different amino acid residue, and which polypeptide is useful in practicing the present invention.

Conservative amino acid substitutions are well-known in the art. For example, it can reasonably be expected that one or more amino acid residues of a Neospora DHFR-TS protein can be conservatively substituted with an amino acid residue of similar charge, size or polarity, with the resulting polypeptide remaining useful in practicing the present invention. Rules for making such substitutions include those described by Dayhof, M. D., 1978, Nat. Biomed. Res. Found., Washington, D.C., Vol. 5, Sup. 3, among others. More specifically, conservative amino acid substitutions are those that generally take place within a family of amino acids that are related in their side chains. Genetically encoded amino acids are generally divided into four groups: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan and tyrosine are also jointly classified as aromatic amino acids. One or more replacements within any particular group, e.g., of a leucine by isoleucine or valine, or of an aspartate by glutamate, or of a threonine by serine, or of any other amino acid residue by a structurally related amino acid residue, will generally have an insignificant effect on the usefulness of the resulting polypeptide in practicing the present invention.

As used herein, a protein or polypeptide is considered "useful in practicing the present invention" where the protein or polypeptide can be used for any one or more of a variety of purposes including, e.g., to screen for inhibitory agents that specifically target either of the two enzymatic domains of the DHFR-TS protein of Neospora, or to raise antibodies against either the whole protein or one of the two enzymatic domains therein.

The present invention further provides a polynucleotide molecule consisting of a nucleotide sequence that is a substantial portion of any of the aforementioned polynucleotide molecules. As used herein, a "substantial portion" of any of the aforementioned polynucleotide molecules means a polynucleotide molecule consisting of less than the complete nucleotide sequence of the particular DHFR-TS-related polynucleotide molecule, but comprising at least about 30%, and more preferably at least about 50%, of the nucleotide sequence of the DHFR-TS-related polynucleotide molecule, and that is useful in practicing the present invention, as usefulness is defined above for polynucleotide molecules. In a preferred embodiment, the polynucleotide molecule consists of a nucleotide sequence that encodes a peptide fragment of any of the aforementioned Neospora DHFR-TS proteins or substantially homologous polypeptides, such as a polypeptide consisting of the DHFR domain or the TS domain of the DHFR-TS protein. As used herein, the term "peptide fragment" refers to a polypeptide consisting of one or more sub-sequences of the complete amino acid sequence of the Neospora DHFR-TS protein or substantially homologous polypeptide, which sub-sequences are shorter in length than the full-length molecule, and where the resulting peptide fragment is useful in the practice of the present invention, as usefulness is defined above for polypeptides. Thus, where the full-length molecule is represented as having "n" amino acid residues, a peptide fragment thereof would be any polypeptide smaller than the full-length sequence, including a polypeptide having n-1 amino acid residues, where such polypeptide is useful in the practice of the present invention. Peptide fragments of the present invention are preferably at least about 10 amino acid residues in length. In a non-limiting embodiment, the peptide fragment consists of the DHFR domain or the TS domain of the Neospora DHFR-TS protein.

Where the peptide fragment consists of more than one sub-sequence of a DHFR-TS protein or substantially homologous polypeptide, the polynucleotide molecule encoding the peptide fragment may be fashioned so that the several sub-sequences are brought together and made contiguous to each other in the peptide fragment where the corresponding sub-sequences were non-contiguous in the full-length protein or polypeptide. Furthermore, a polynucleotide molecule encoding a peptide fragment may be fashioned so that different sub-sequences comprising the peptide fragment are arranged in a different relative order to each other compared to the full-length protein or polypeptide, or so that the encoded peptide fragment comprises multiple copies of a specific sub-sequence. For example, the polynucleotide molecule may encode multiple copies of either the DHFR domain or the TS domain, epitopic regions selected therefrom, or a combination thereof.

The present invention further encompasses polynucleotide molecules encoding a full-length (n) polypeptide in which sub-sequences of the native protein have been rearranged relative to one another, in addition to polynucleotide molecules encoding polypeptides that are larger than the native protein, including polypeptides up to about 2n in length. Such polypeptides may comprise multiple copies of either the whole protein, individual domains, epitopic regions, or some combination thereof.

In addition to the nucleotide sequences of any of the aforementioned DHFR-TS-related polynucleotide molecules, polynucleotide molecules of the present invention can further comprise, or alternatively may consist of, one or more nucleotide sequences selected from the sequences that naturally flank the DHFR-TS gene in situ in *N. caninum*, such as, e.g., the flanking nucleotide sequences shown in SEQ ID NO:1, or portions thereof.

The sequences of the polynucleotide molecules of the present invention further provide the information necessary to construct oligonucleotide molecules that can be used as primers in amplification techniques or as probes in differential disease diagnosis, and that can be readily designed by the skilled artisan in light of this disclosure. Such oligonucleotides are preferably at least about 15 nucleotides in length. Amplification can be carried out using suitably designed oligonucleotides by applying standard techniques such as, e.g., the polymerase chain reaction (PCR) which is described, among other places, in Innis et al., (eds), 1995, *PCR Strategies*, Academic Press, Inc., San Diego; and Erlich (ed), 1992, *PCR Technology*, Oxford University Press, New York, which publications are incorporated herein by reference. Regarding diagnostics, oligonucleotides of the present invention can be used in PCR amplification to detect the presence of Neospora-specific polynucleotide molecules in a sample of animal tissue or fluid, such as brain tissue, lung tissue, placental tissue, blood, cerebrospinal fluid, mucous, urine, amniotic fluid, etc. The production of a specific amplification product can be used to support a diagnosis of Neospora infection, while lack of an amplified product may point to a lack of infection. Generally, for PCR, a mixture comprising suitably designed primers, a template comprising the nucleotide sequence to be amplified, and appropriate PCR enzymes and buffers, is prepared and processed according to standard protocols to amplify a specific Neospora DHFR-TS polynucleotide molecule of the template or a portion thereof. Other amplification techniques known in the art, e.g., the ligase chain reaction, may alternatively be used.

All subsequent references to a "polynucleotide molecule" are intended to include any of the aforementioned polynucleotide molecules of the present invention, including polynucleotide molecules comprising the nucleotide sequence of the DHFR-TS gene as shown in SEQ ID NO:1 from about nt 2405 to about nt 8199, or as present in phage λNclDHFRTS (ATCC Accession No. 209512), or the nucleotide sequence of SEQ ID NO:2; polynucleotide molecules that are substantially homologous to a polynucleotide molecule comprising the nucleotide sequence of the DHFR-TS gene as shown in SEQ ID NO:1 from about nt 2405 to about nt 8199, or the nucleotide sequence of the DHFR-TS gene as present in phage λNclDHFRTS (ATCC Accession No. 209512), or the nucleotide sequence of SEQ ID NO:2; polynucleotide molecules comprising a nucleotide sequence encoding a polypeptide that is substantially homologous to a Neospora DHFR-TS protein having the amino acid sequence of SEQ ID NO:3, or the amino acid sequence of a DHFR-TS protein as encoded by the DHFR-TS gene as present in phage λNclDHFRTS (ATCC Accession No.

209512); and polynucleotide molecules consisting of a nucleotide sequence that is a substantial portion of any of the aforementioned polynucleotide molecules, including polynucleotide molecules consisting of a nucleotide sequence that encodes a peptide fragment of any of the aforementioned Neospora DHFR-TS proteins or substantially homologous polypeptides, unless otherwise specifically indicated.

All subsequent references to a "DHFR-TS protein," "protein," or "polypeptide" are intended to include a protein having the amino acid sequence of SEQ ID NO:3, or the amino acid sequence of a DHFR-TS protein as encoded by the DHFR-TS gene as present in phage λNclDHFRTS (ATCC Accession No. 209512); polypeptides that are substantially homologous to any of the aforementioned proteins; and peptide fragments of any of the aforementioned proteins or polypeptides, unless otherwise specifically indicated.

Production and manipulation of the polynucleotide and oligonucleotide molecules of the invention are within the skill in the art and can be carried out according to known genetic techniques which are described, among other places, in Maniatis et al., 1989, *Molecular Cloning, A Laboratory Manual*, Cold Spring Harbor Laboratory Press, Cold Spring Harbor, N.Y.; Ausubel et al., 1989, above; Sambrook et al., 1989, *Molecular Cloning: A Laboratory Manual*, 2d ed., Cold Spring Harbor Laboratory Press, Cold Spring Harbor, N.Y.; Innis et al., 1995, above; and Erlich, 1992, above, which are incorporated herein by reference.

4.2. Recombinant Expression Systems
4.2.1. Cloning And Expression Vectors

The present invention further provides recombinant cloning and expression vectors comprising a polynucleotide molecule of the present invention. In a non-limiting embodiment, a cloning vector provided by the present invention is phage λNclDHFRTS (ATCC Accession No. 209512), which comprises a polynucleotide molecule having a nucleotide sequence of the complete DHFR-TS gene of *N. caninum* strain NC-1.

Expression vectors of the present invention are preferably constructed so that the polynucleotide molecule is in operative association with one or more regulatory elements necessary for transcription and translation. The expression vector is used in an expression system, such as a transformed host cell, to produce a recombinantly-expressed DHFR-TS protein.

As used herein, the term "regulatory element" includes but is not limited to nucleotide sequences that encode inducible and non-inducible promoters, enhancers, operators, and other elements known in the art which serve to drive and/or regulate expression of a polynucleotide coding sequence. As used herein, the DHFR-TS coding sequence is in "operative association" with one or more regulatory elements where the regulatory elements effectively regulate and provide for the transcription of the DHFR-TS coding sequence or the translation of its mRNA, or both.

Methods are well-known in the art for constructing expression vectors containing particular coding sequences in operative association with appropriate regulatory elements, and these may be used to practice the present invention. Such methods include in vitro recombinant techniques, synthetic techniques, and in vivo genetic recombination, as described, among other places, in Maniatis et al., 1989, above; Ausubel et al., 1989, above; and Sambrook et al., 1989, above.

A variety of expression vectors are known in the art that can be utilized to express the coding sequence of a polynucleotide molecule of the present invention, including recombinant bacteriophage DNA, plasmid DNA and cosmid DNA expression vectors containing the DHFR-TS coding sequence for transformation of bacteria or yeast; and recombinant virus expression vectors such as, e.g., baculovirus, containing the DHFR-TS coding sequence for transfection of insect cells, or adenovirus or vaccinia virus, containing the DHFR-TS coding sequence for transfection of mammalian cells, among others.

Typical prokaryotic expression vector plasmids that can be engineered to contain a polynucleotide molecule of the present invention include pUC8, pUC9, pBR322 and pBR329 (Biorad Laboratories, Richmond, Calif.), and pPL and pKK223 (Pharmacia, Piscataway, N.J.), among others.

Typical eukaryotic expression vectors that can be engineered to contain a polynucleotide molecule of the present invention include an ecdysone-inducible mammalian expression system (Invitrogen, Carlsbad, Calif.), cytomegalovirus promoter-enhancer-based systems (Promega, Madison, Wis.; Stratagene, La Jolla, Calif.; Invitrogen), and baculovirus-based expression systems (Promega), among others.

The regulatory elements of these and other vectors can vary in their strength and specificities. Depending on the host/vector system utilized, any of a number of suitable transcription and translation elements can be used. For instance, when cloning in mammalian cell systems, promoters isolated from the genome of mammalian cells, e.g., mouse metallothionein promoter, or from viruses that grow in these cells, e.g., vaccinia virus 7.5K promoter or Moloney murine sarcoma virus long terminal repeat, may be used. Promoters obtained by recombinant DNA or synthetic techniques may also be used to provide for transcription of the inserted sequence. In addition, expression from certain promoters can be elevated in the presence of particular inducers, e.g., zinc and cadmium ions for metallothionein promoters.

Non-limiting examples of transcriptional regulatory regions or promoters include for bacteria, the β-gal promoter, the T7 promoter, the TAC promoter, λ left and right promoters, trp and lac promoters, trp-lac fusion promoters, etc.; for yeast, glycolytic enzyme promoters, such as ADH-I and -II promoters, GPK promoter, PGI promoter, TRP promoter, etc.; for mammalian cells, SV40 early and late promoters, adenovirus major late promoters, etc.

Specific initiation signals are also required for sufficient translation of inserted DHFR-TS coding sequences. These signals typically include an ATG initiation codon and adjacent sequences. In cases where the polynucleotide molecule of the present invention including its own initiation codon and adjacent sequences are inserted into the appropriate expression vector, no additional translation control signals may be needed. However, in cases where only a portion of a coding sequence is inserted, exogenous translational control signals, including the ATG initiation codon, may be required. These exogenous translational control signals and initiation codons can be obtained from a variety of sources, both natural and synthetic. Furthermore, the initiation codon must be in phase with the reading frame of the DHFR-TS coding region to ensure in-frame translation of the entire insert.

Fusion protein expression vectors may be used to express a DHFR-TS fusion protein. The purified fusion protein may be used to raise antisera against the DHFR-TS protein, to study the biochemical properties of the DHFR-TS protein, to engineer DHFR-TS fusion proteins with different enzymatic activities, or to aid in the identification or purification of the expressed DHFR-TS protein. Possible fusion protein expression vectors include but are not limited to vectors incorporating sequences that encode β-galactosidase and trpE fusions, maltose-binding protein fusions, glutathione-S-transferase fusions and polyhistidine fusions (carrier regions). Methods known in the art can be used to construct expression vectors encoding such DHFR-TS fusion proteins.

As mentioned above, the fusion protein can be useful to aid in purification of the expressed protein. For example, DHFR-TS-maltose-binding protein fusions can be purified using amylose resin; DHFR-TS-glutathione-S-transferase fusion proteins can be purified using glutathione-agarose beads; and DHFR-TS-polyhistidine fusions can be purified using divalent nickel resin. Alternatively, antibodies against a carrier protein or peptide can be used for affinity chromatography purification of the fusion protein. For example, a nucleotide sequence coding for the target epitope of a monoclonal antibody can be engineered into the expression vector in operative association with the regulatory elements and situated so that the expressed epitope is fused to the DHFR-TS protein. For example, a nucleotide sequence coding for the FLAG™ epitope tag (International Biotechnologies Inc.), which is a hydrophilic marker peptide, can be inserted by standard techniques into the expression vector at a point corresponding, e.g., to the carboxyl terminus of the DHFR-TS protein. The expressed DHFR-TS protein-FLAG™ epitope fusion product can then be detected and affinity-purified using commercially available anti-FLAG™ antibodies.

The expression vector can also be engineered to contain polylinker sequences which encode specific protease cleavage sites so that the expressed DHFR-TS protein can be released from the carrier region or fusion partner by treatment with a specific protease. For example, the fusion protein vector can include DNA sequences encoding thrombin or factor Xa cleavage sites, among others.

A signal sequence upstream from, and in reading frame with, the DHFR-TS coding region can be engineered into the expression vector by known methods to direct the trafficking and secretion of the expressed protein. Non-limiting examples of signal sequences include those from α-factor, immunoglobulins, outer membrane proteins, penicillinase, and T-cell receptors, among others.

To aid in the selection of host cells transformed or transfected with an expression vector of the present invention, the expression vector can be engineered to further comprise a coding sequence for a reporter gene product or other selectable marker. Such a coding sequence is preferably in operative association with the regulatory element coding sequences, as described above. Reporter genes which are useful in the invention are well-known in the art and include those encoding chloramphenicol acetyltransferase (CAT), green fluorescent protein, firefly luciferase, and human growth hormone, among others. Nucleotide sequences encoding selectable markers are well-known in the art, and include those that encode gene products conferring resistance to antibiotics or anti-metabolites, or that supply an auxotrophic requirement. Examples of such sequences include those that encode thymidine kinase activity, or resistance to methotrexate, ampicillin, kanamycin, chloramphenicol, zeocin, pyrimethamine, aminoglycosides, or hygromycin, among others.

4.2.2. Transformation Of Host Cells

The present invention provides transformed host cells comprising a polynucleotide molecule or recombinant expression vector of the present invention, and cell lines derived therefrom. Host cells useful in the practice of the invention can be eukaryotic, although prokaryotic cells are preferred. Such transformed host cells include but are not limited to microorganisms, such as bacteria transformed with recombinant bacteriophage DNA, plasmid DNA or cosmid DNA expression vectors; or yeast transformed with a recombinant expression vector; or animal cells, such as insect cells infected with a recombinant virus expression vector, e.g., baculovirus, or mammalian cells infected with a recombinant virus expression vector, e.g., adenovirus or vaccinia virus, among others.

Bacterial cells may be used as host cells. For example, a strain of E. coli may be used, such as, e.g., the DH5α strain, available from the ATCC, Rockville, Md., USA (Accession No. 31343), or from Stratagene (La Jolla, Calif.). Eukaryotic host cells include yeast cells, although mammalian cells, such as from a mouse, hamster, cow, monkey, or human cell line, may also be utilized effectively. Examples of eukaryotic host cells that may be used to express the recombinant protein of the invention include Chinese hamster ovary (CHO) cells (e.g., ATCC Accession No. CCL-61), NIH Swiss mouse embryo cells NIH/3T3 (e.g., ATCC Accession No. CRL-1658), Madin-Darby bovine kidney (MDBK) cells (ATCC Accession No. CCL-22), and thymidine kinase-deficient cells, e.g., L-M (TK$^-$) (ATCC Accession No. CCL-1.3) and tk$^-$-ts 13 (ATCC Accession No. CRL-1632).

The recombinant expression vector of the invention is preferably transformed or transfected into one or more host cells of a substantially homogeneous culture of cells. The expression vector is generally introduced into host cells in accordance with known techniques, such as, e.g., by calcium phosphate precipitation, calcium chloride treatment, microinjection, electroporation, transfection by contact with a recombined virus, liposome-mediated transfection, DEAE-dextran transfection, transduction, conjugation, or microprojectile bombardment, among others. Selection of transformants may be conducted by standard procedures, such as by selecting for cells expressing a selectable marker, e.g., antibiotic resistance, associated with the recombinant expression vector.

Once the expression vector is introduced into the host cell, the integration and maintenance of the polynucleotide molecule of the present invention, either in the host cell genome or episomally, can be confirmed by standard techniques, e.g., by Southern hybridization analysis, restriction enzyme analysis, PCR analysis including reverse transcriptase PCR (rt-PCR), or by immunological assay to detect the expected protein product. Host cells containing and/or expressing the polynucleotide molecule of the present invention may be identified by any of at least four general approaches, which are well-known in the art, including: (i) DNA-DNA, DNA-RNA, or RNA-antisense RNA hybridization; (ii) detecting the presence of "marker" gene functions; (iii) assessing the level of transcription as measured by the expression, e.g., of DHFR-TS-specific mRNA transcripts in the host cell; or (iv) detecting the presence of mature polypeptide product, e.g., by immunoassay or by detecting a DHFR enzymatic activity such as, e.g., the conversion of dihydrofolate to tetrahydrofolate catalyzed by NADPH oxidation, or a TS enzymatic activity such as, e.g., the conversion of deoxyuridine monophosphate to deoxythymidine monophosphate, as known in the art.

4.2.3. Expression And Purification Of Recombinant Polypeptides

Once the polynucleotide molecule of the present invention has been stably introduced into an appropriate host cell, the transformed host cell is clonally propagated, and the resulting cells are grown under conditions conducive to the maximum production of the encoded DHFR-TS protein. Such conditions typically include growing transformed cells to high density. Where the expression vector comprises an inducible promoter, appropriate induction conditions such as, e.g., temperature shift, exhaustion of nutrients, addition of gratuitous inducers (e.g., analogs of carbohydrates, such as isopropyl-β-D-thiogalactopyranoside (IPTG)), accumulation of excess metabolic by-products, or the like, are employed as needed to induce expression.

Where the expressed DHFR-TS protein is retained inside the host cells, the cells are harvested and lysed, and the product purified from the lysate under extraction conditions known in the art to minimize protein degradation such as, e.g., at 4° C., or in the presence of protease inhibitors, or both. Where the expressed DHFR-TS protein is secreted from the host cells, the exhausted nutrient medium may simply be collected and the protein isolated therefrom.

The expressed DHFR-TS protein can be purified from cell lysates or culture medium, as appropriate, using standard methods, including but not limited to one or more of the following methods: ammonium sulfate precipitation, size fractionation, ion exchange chromatography, HPLC, density centrifugation, and affinity chromatography. Where the expressed DHFR-TS protein exhibits enzymatic activity, e.g., the ability to convert either dihydrofolate to tetrahydrofolate as catalyzed by NADPH oxidation (DHFR), or deoxyuridine monophosphate to deoxythymidine monophosphate (TS), increasing purity of the preparation can be monitored at each step of the purification procedure by use of an appropriate assay, as known in the art. If the expressed protein lacks biological activity, it may be detected as based, e.g., on size, or reactivity with an antibody otherwise specific for the DHFR-TS protein, or by the presence of a fusion tag. For use in practicing the present invention, the recombinantly-expressed DHFR-TS protein can be in an unpurified state, as produced in culture or as present in a cell lysate, or can be partially or substantially purified therefrom.

Thus, the present invention provides a method of preparing a DHFR-TS protein, comprising culturing a host cell transformed with a recombinant expression vector, said recombinant expression vector comprising a polynucleotide molecule of the present invention in operative association with one or more regulatory elements, under conditions conducive to the expression of the DHFR-TS protein, and recovering the DHFR-TS protein from the cell culture.

The present invention further provides an isolated Neospora DHFR-TS protein comprising the amino acid sequence shown as SEQ ID NO:3, or a protein comprising the amino acid sequence of the DHFR-TS protein encoded by the DHFR-TS gene present in phage λNclDHFRTS (ATCC Accession No. 209512); substantially homologous polypeptides thereof;

and peptide fragments of the aforementioned proteins and polypeptides. For example, peptide fragments of the invention may consist of the DHFR domain or the TS domain of the Neospora DHFR-TS protein. An amino acid sequence of the predicted DHFR domain of the Neospora DHFR-TS protein is shown in SEQ ID NO:3 from about amino acid residue 1 to about amino acid residue 323; an amino acid sequence of the predicted TS domain is from about amino acid residue 324 to amino acid residue 612.

4.3. Use Of DHFR-TS Proteins

Once a DHFR-TS protein of sufficient purity has been obtained, it can be characterized by standard methods, including by SDS-PAGE, size exclusion chromatography, amino acid sequence analysis, biological activity, etc. The DHFR-TS protein can be further characterized using hydrophilicity analysis (see, e.g., Hopp and Woods, 1981, Proc. Natl. Acad. Sci. USA 78:3824), or analogous software algorithms, to identify hydrophobic and hydrophilic regions. Structural analysis can be carried out to identify regions of the DHFR-TS protein that assume specific secondary structures. Biophysical methods such as X-ray crystallography (Engstrom, 1974, Biochem. Exp. Biol. 11: 7–13), computer modeling (Fletterick and Zoller (eds), 1986, in: *Current Communications in Molecular Biology*, Cold Spring Harbor Laboratory, Cold Spring Harbor, N.Y.), and nuclear magnetic resonance (NMR) can be used to map and study sites of interaction between the DHFR-TS protein and any of its substrates. Information obtained from these studies can be used to design more effective deletion mutants and vaccine compositions, or to design or select therapeutic or pharmacologic compounds that can specifically block the enzymatic activity of either the DHFR or TS domains of the Neospora DHFR-TS protein in vivo.

Isolated DHFR-TS proteins of the invention, recombinant or otherwise, are useful for a variety of purposes. For example, the protein may be used to screen for inhibitory agents that specifically block the enzymatic activity of either the DHFR or TS domains. Such screening procedures are well-known in the art. The DHFR-TS proteins of the invention can also be used as antigens to raise either polyclonal or monoclonal antibodies, as described below, that react specifically with the protein. Such antibodies may be useful, e.g., as affinity reagents with which to purify native or recombinant DHFR-TS protein, or as diagnostic reagents to detect the presence of a Neospora-specific DHFR-TS protein in cell, tissue or fluid samples from an animal, such as, e.g., by ELISA or Western blot assays.

Antibodies can be raised against a DHFR-TS protein and isolated utilizing known methods. Various host animals, including pigs, cows, horses, rabbits, goats, sheep, and mice, can be immunized with the partially or substantially purified antigen. An adjuvant, such as described below, can be used to enhance antibody production. Polyclonal antibodies can be obtained from the serum of an immunized animal and tested for anti-DHFR-TS protein specificity using standard techniques. Alternatively, monoclonal antibodies against the DHFR-TS protein can be prepared using any technique which provides for the production of antibody molecules by continuous cell lines in culture. These include but are not limited to the hybridoma technique originally described by Kohler and Milstein (Nature, 1975, 256: 495–497); the human B-cell hybridoma technique (Kosbor et al., 1983, Immunology Today 4:72; Cote et al., 1983, Proc. Natl. Acad. Sci. USA 80: 2026–2030); and the EBV-hybridoma technique (Cole et al., 1985, *Monoclonal Antibodies and Cancer Therapy*, Alan R. Liss, Inc., pp. 77–96). Alternatively, techniques described for the production of single chain antibodies (see, e.g., U.S. Pat. No. 4,946,778) can be adapted to produce DHFR-TS antigen-specific single chain antibodies. These publications are incorporated herein by reference.

Antibody fragments that contain specific binding sites for a DHFR-TS antigen are also encompassed within the present invention, and can be generated by known techniques. Such fragments include but are not limited to F(ab')$_2$ fragments which can be generated by pepsin digestion of an intact antibody molecule, and Fab fragments which can be generated by reducing the disulfide bridges of the F(ab')$_2$ fragments. Alternatively, Fab expression libraries can be constructed (Huse et al., 1989, Science 246: 1275–1281) to allow rapid identification of Fab fragments having the desired specificity to the DHFR-TS antigen.

Techniques for the production of monoclonal antibodies and antibody fragments are well-known in the art, and are additionally described, among other places, in Harlow and Lane, 1988, Antibodies: A Laboratory Manual, Cold Spring Harbor Laboratory, and in J. W. Goding, 1986, Monoclonal Antibodies: Principles and Practice, Academic Press, London, which are incorporated herein by reference.

4.4. Targeted Mutation Of The Neospora DHFR-TS Gene 4.4.1. Genetic Constructs Based on the disclosure of the polynucleotide molecules of the present invention, genetic constructs can be prepared for use in disabling a Neospora DHFR-TS gene. The Neospora DHFR-TS gene can be disabled using an appropriately designed genetic construct in combination with genetic techniques now known or to be developed in the future. For example, a Neospora DHFR-TS gene can be disabled using a genetic construct of the present invention that functions to: (a) delete all or a portion of the DHFR-TS gene; or (b) replace a portion of the DHFR-TS gene with a different nucleotide sequence; or (c) insert into the DHFR-TS gene one or more nucleotides, or an oligonucleotide molecule or a polynucleotide molecule which may comprise a nucleotide sequence from Neospora or from another source. Neospora cells in which a DHFR-TS gene has been disabled are useful in practicing the present invention where disabling the DHFR-TS gene reduces the pathogenicity of the Neospora cells carrying the disabled DHFR-TS gene compared to cells of the same strain of Neospora where the DHFR-TS gene has not been so disabled, and where such Neospora cells carrying the disabled DHFR-TS gene can be used in a vaccine composition, particularly in a modified live vaccine, to induce a protective response in a mammal against neosporosis.

In a non-limiting embodiment, the genetic construct of the present invention is used to disable a wild-type Neospora DHFR-TS gene by replacement of the nucleotide sequence of the wild-type DHFR-TS gene or a portion thereof with a mutated Neospora DHFR-TS gene or portion thereof. Mutated Neospora DHFR-TS gene sequences for use in such a genetic construct can be produced by any of a variety of known methods, including by use of error-prone PCR, or by cassette mutagenesis. For example, oligonucleotide-directed mutagenesis can be employed to alter the ORF sequence of the wild-type Neospora DHFR-TS gene in a defined way, e.g., to introduce a frame-shift or a termination codon into specific regions within the sequence. Alternatively or additionally, a mutated nucleotide sequence for use in the genetic construct of the present invention can be prepared by insertion into the Neospora DHFR-TS gene of one or more nucleotides, oligonucleotide molecules or polynucleotide molecules, or by replacement of a portion of the Neospora DHFR-TS gene with one or more nucleotides, oligonucleotide molecules or polynucleotide molecules. Such oligonucleotide molecules or polynucleotide molecules can be obtained from any naturally occurring source or can be synthetic. The inserted sequence can serve simply to disrupt the reading frame of the Neospora DHFR-TS gene, or can also encode a heterologous gene product such as a selectable marker. Random mutagenesis can also be used to produce a mutated Neospora DHFR-TS gene sequence for use in a genetic construct of the present invention. Random mutagenesis can be carried out by any techniques now known or to be developed in the future such as, e.g., by exposing cells carrying a Neospora DHFR-TS gene to ultraviolet radiation or x-rays, or to chemical mutagens such as N-methyl-N'-nitrosoguanidine, ethyl methane sulfonate, nitrous acid or nitrogen mustards, and then selecting for cells carrying a mutation in the DHFR-TS gene. See, e.g., Ausubel, 1989, above, for a review of mutagenesis techniques.

Mutations to produce modified Neospora cells that are useful in practicing the present invention, as defined above, can occur anywhere in the Neospora DHFR-TS gene, including in the ORF, or in the promoter region, or in any other sequences that flank the gene or ORF.

Such Neospora cells can be mutants in which a modified form of the protein encoded by the Neospora DHFR-TS gene is produced, or in which no such protein is produced at all. In a preferred embodiment, such Neospora cells exhibit a dhfr$^-$, or a ts$^-$, or a dhfr$^-$-ts$^-$ mutant phenotype (hereinafter referred to collectively as a dhfr$^-$-ts$^-$ phenotype). In addition, such Neospora cells can be null, conditional or leaky mutants.

Alternatively, a genetic construct of the present invention can comprise nucleotide sequences that naturally flank the Neospora DHFR-TS gene or ORF in situ, as selected from the flanking sequences shown in SEQ ID NO:1, with few or no nucleotide sequences present from the coding region of the gene itself. Such a genetic construct would be useful, e.g., to delete the entire gene or ORF.

In a preferred embodiment, a genetic construct of the present invention comprises a polynucleotide molecule that can be used to disable a Neospora DHFR-TS gene, comprising: (a) a polynucleotide molecule having a nucleotide sequence that is otherwise the same as a nucleotide sequence encoding a DHFR-TS protein from *N. caninum*, but which nucleotide sequence further comprises one or more disabling mutations; or (b) a polynucleotide molecule consisting of nucleotide sequences that naturally flank the ORF of a Neospora DHFR-TS gene in situ. Once transformed into cells of a strain of Neospora, the polynucleotide molecule of the genetic construct is specifically targeted to the Neospora DHFR-TS gene, e.g., by homologous recombination, and thereby either replaces the gene or portion thereof or inserts into the gene. As a result of this recombination event, the Neospora DHFR-TS gene otherwise native to that particular strain of Neospora is disabled.

Methods for carrying out homologous gene replacement in parasitic protozoans are known in the art, and are described, among other places, in Cruz and Beverley, 1990, Nature 348:171–173; Cruz et al., 1991, Proc. Natl. Acad. Sci. USA 88:7170–7174; Donald and Roos, 1994, Mol. Biochem. Parasitol. 63:243–253; and Titus et al., 1995, Proc. Natl. Acad. Sci. USA 92:10267–10271, all of which are incorporated herein by reference.

For targeted gene mutation through homologous recombination, the genetic construct is preferably a plasmid, either circular or linearized, comprising a mutated nucleotide sequence as described above. In a non-limiting embodiment, at least about 200 nucleotides of the mutated sequence are used to specifically target the genetic construct of the present invention to the Neospora DHFR-TS gene for homologous recombination, although shorter lengths of nucleotides can also be effective. In addition, the plasmid preferably comprises an additional nucleotide sequence encoding a reporter gene product or other selectable marker that is constructed so that it will insert into the Neospora genome in operative association with the regulatory element coding sequences of the native Neospora DHFR-TS gene.

Reporter genes that can be used in practicing the invention are well-known in the art and include those encoding CAT, green fluorescent protein, and β-galactosidase, among others. Nucleotide sequences encoding selectable markers are also well-known in the art, and include those that encode gene products conferring resistance to antibiotics or antimetabolites, or that supply an auxotrophic requirement. Examples of such sequences include those that encode pyrimethamine resistance, or neomycin phosphotransferase (which confers resistance to aminoglycosides), or hygromycin phosphotransferase (which confers resistance to hygromycin).

Methods that can be used for creating the genetic constructs of the present invention are well-known in the art, and include in vitro recombinant techniques, synthetic techniques, and in vivo genetic recombination, as described, among other places, in Maniatis et al., 1989, above; Ausubel et al., 1989, above; and Sambrook et al., 1989, above.

Neospora cells can be transformed or transfected with a genetic construct of the present invention in accordance with known techniques, such as, e.g., by electroporation. Selection of transformants can be carried out using standard techniques, such as by selecting for cells expressing a selectable marker associated with the construct. Identification of transformants in which a successful recombination event has occurred, and the particular target gene has been disabled, can be carried out by genetic analysis, such as by Southern blot analysis, or by Northern analysis to detect a lack of mRNA transcripts encoding the DHFR-TS protein, or by the appearance of a novel phenotype, such as reduced pathogenicity, or cells lacking the DHFR-TS protein, as determined, e.g., by immunological analysis, or some combination thereof.

Neospora cells that can be modified according to the present invention are preferably tachyzoites, but can alternatively be bradyzoites or oocysts. Although cells in certain stages of the Neospora life cycle are diploid, tachyzoites are haploid. Thus, the use of tachyzoites in the production of modified Neospora cells expressing the appropriate mutant phenotype is preferred because tachyzoites require only a single successful recombination event to disrupt the particular Neospora gene. Alternatively, in diploid cells of Neospora, two alleles must be disrupted for each gene. This can be accomplished by sequentially targeting the first allele and then the second allele with genetic constructs bearing two different selectable markers.

In a further non-limiting embodiment, the genetic construct of the present invention can additionally comprise a different gene or coding region from Neospora or from a different pathogen that can infect the animal, which gene or coding region encodes an antigen useful to induce a separate and distinct protective immune response in the animal upon vaccination with the modified live Neospora cells of the present invention. This additional gene or coding region can be further engineered to contain a signal sequence that leads to secretion of the encoded antigen from the modified live Neospora cell, thereby allowing for the antigen to be displayed to the immune system of the vaccinated animal.

The present invention thus provides modified live Neospora cells in which the DHFR-TS gene has been disrupted. In addition, the present invention provides a method of preparing modified live Neospora cells, comprising: (a) transforming cells of Neospora with a genetic construct of the invention; (b) selecting transformed cells in which the DHFR-TS gene has been disrupted by the genetic construct; and (c) selecting from among the cells of step (b) those cells that can be used in a vaccine to protect a mammal against neosporosis.

4.4.2. Culturing Neospora Cells

Neospora cells for use in the present invention can be cultured and maintained in vitro by infecting any receptive cell line, preferably a mammalian cell line, with tachyzoites according to known techniques described in the art. Mammalian cell lines in which tachyzoites of Neospora can be cultured include, e.g., human foreskin fibroblasts (Lindsay et al., 1993, Am. J. Vet. Res. 54:103–106), bovine cardiopulmonary aortic endothelial cells (Marsh et al., 1995, above), bovine monocytes (Lindsay and Dubey, 1989, above), and monkey kidney cells, among others. For example, tachyzoites of *N. caninum* can be cultured in monolayers of Hs68 human foreskin fibroblast cells (ATCC Accession No. CRL-1635) (Lindsay et al., 1993, above); and MARC145 monkey kidney cells infected with tachyzoites of *N. caninum* strain NC-1 for use in the present invention are on deposit with the ATCC (Accession No. 12231). Bradyzoites can be similarly cultured and manipulated.

Mammalian cell cultures can be grown, and cell cultures that have been infected with Neospora can be maintained, in any of several types of culture media described in the art. For example, stationary monolayer cultures of bovine cardiopulmonary aortic endothelial cells infected with tachyzoites of *N. caninum* can be grown in Dulbecco's Minimum Essential Medium (DMEM: Gibco Laboratories, N.Y.), supplemented with 10% (v/v) heat-inactivated fetal bovine serum (FBS) or adult equine serum (ES), 2 mM L-glutamine, 50 U/ml penicillin, and 50 μg/ml streptomycin (Conrad et al., 1993, above). Monolayers of Hs68 human foreskin fibroblast cells can be maintained in RPMI 1640 containing 2% (v/v) FBS, 1.0 mM sodium pyruvate, $1\times10^4$ U/ml penicillin, $1\times10^4$ μg/ml streptomycin, $5\times10^{-2}$ mM 2-mercaptoethanol and 0.3 mg/ml L-glutamine (maintenance medium). Monolayer cultures of Hs68 human foreskin fibroblast cells infected with Neospora can be maintained in identical media, but in which the FBS is increased to 10% (v/v) (growth medium).

Neospora-infected monolayer cultures of mammalian cells are typically maintained under standard tissue culture conditions such as, e.g., at 37° C. and 5% $CO_2$. Tachyzoites are typically passaged to uninfected monolayer cultures when 70–90% of the mammalian cells in the culture have become infected, which can be determined microscopically using standard techniques. Tachyzoites can be collected from the infected mammalian cell cultures by lysing the host cells using any standard technique and collecting the tachyzoites, e.g., by filtration or by centrifugation.

Cells of Neospora that have been modified according to the present invention, and which exhibit a $dhfr^-$-$ts^-$ phenotype, can be cultured in mammalian cells, as described above, in medium containing thymidine.

4.5. Anti-Neospora Vaccines

The present invention provides a vaccine against neosporosis, comprising an immunologically effective amount of modified live Neospora cells, such as, e.g., the aforementioned $dhfr^-$-$ts^-$ null mutants, and a veterinarily acceptable carrier.

The present invention further provides a method of preparing a vaccine that protects a mammal against neosporosis, comprising preparing modified live cells, such as, e.g., those exhibiting a $dhfr^-$-$ts^-$ phenotype prepared as described above, and combining an immunologically effective amount of the modified live cells with a veterinarily acceptable carrier in a form suitable for administration to the mammal.

As used herein, the term "immunologically effective amount" refers to that amount of modified live Neospora cells of the present invention capable of inducing a protective response against neosporosis when administered to a member of a mammalian species after either a single administration, or after multiple administrations.

The phrase "capable of inducing a protective response" is used broadly herein to include the induction or enhancement of any immune-based response in the animal in response to vaccination, including either an antibody or cell-mediated immune response, or both, that serves to protect the vaccinated animal against neosporosis. The terms "protective response" and "protect" as used herein refer not only to the absolute prevention of neosporosis or absolute prevention of infection by a neosporosis-causing pathogen, but also to any detectable reduction in the degree or rate of infection by such a pathogen, or any detectable reduction in the severity of the disease or in any symptom or condition resulting from infection by the pathogen, including, e.g., any detectable reduction in the rate of formation or in the absolute number of lesions formed in one or more tissues, or any detectable reduction in the occurrence of abortion, or the transmission of infection from a pregnant mammal to its fetus, or from a mammal parent to its offspring, in the vaccinated animal as compared to an unvaccinated infected animal of the same species.

The vaccine can simply comprise an aliquot of culture fluid containing modified live Neospora cells, either free in the medium or residing in mammalian host cells, or a combination of both, which is administered directly to the mammal, or can instead comprise modified live Neospora cells combined with a veterinarily acceptable carrier selected from those known in the art as appropriate to the route of administration. It is preferred that at least some degree of viability of the modified live Neospora cells is maintained in the vaccine composition. For example, a vaccine composition of the present invention can be formulated following accepted convention using standard buffers, carriers, stabilizers, diluents, preservatives, and/or solubilizers, and can also be formulated to facilitate sustained release. Diluents can include water, saline, dextrose, ethanol, glycerol, and the like. Additives for isotonicity can include sodium chloride, dextrose, mannitol, sorbitol, and lactose, among others. Stabilizers can include albumin, among others. Suitable other vaccine vehicles and additives which are particularly useful in modified live vaccines are known, or will be apparent, to those skilled in the art,. See, e.g., Remington's *Pharmaceutical Science*, 18th ed., 1990, Mack Publishing, which is incorporated herein by reference.

Modified live Neospora cells that can be used in the vaccine of the present invention are preferably tachyzoites, but can alternatively be bradyzoites or oocysts, or some combination thereof.

The vaccine of the present invention can further comprise one or more additional immunomodulatory components such as, e.g., an adjuvant or cytokine, among others, as long as at least some degree of viability of the modified live Neospora cells in the vaccine composition is maintained. Non-limiting examples of adjuvants which can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block co polymer (CytRx, Atlanta Ga.), QS-21 (Cambridge Biotech Inc., Cambridge Mass.) and SAF-M (Chiron, Emeryville Calif.), AMPHIGEN® adjuvant, saponin, Quil A or other saponin fraction, monophosphoryl lipid A, and Avridine lipid-amine adjuvant. Specific non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 µg/ml Quil A, 100 µg/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween 80 detergent, 2.5% (v/v) ethanol, 100 µg/ml Quil A, and 50 µg/ml cholesterol. Other immunomodulatory agents which can be included in the vaccine include, e.g., one or more interleukins, interferons, or other known cytokines. The vaccine can be stored frozen and thawed prior to administration.

The vaccine of the present invention can optionally be formulated for the sustained release of the modified live Neospora cells, as long as at least some degree of viability of the modified live Neospora cells in the vaccine composition is maintained. Examples of such sustained release formulations include modified live Neospora cells in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including A. Domb et al., 1992, Polymers for Advanced Technologies 3: 279–292, which is incorporated herein by reference. Additional guidance in selecting and using polymers in pharmaceutical formulations can be found in the text by M. Chasin and R. Langer (eds), 1990, "Biodegradable Polymers as Drug Delivery Systems" in: *Drugs and the Pharmaceutical Sciences*, Vol. 45, M. Dekker, NY, which is also incorporated herein by reference. Alternatively, or additionally, the modified live Neospora cells can be microencapsulated to improve administration and efficacy, as long as at least some degree of viability of the modified live Neospora cells in the vaccine composition is maintained. Methods for microencapsulating antigens are well-known in the art, and include techniques described, e.g., in U.S. Pat. 3,137,631; U.S. Pat. No. 3,959,457; U.S. Pat. No. 4,205,060; U.S. Pat. No. 4,606,940; U.S. Pat. No. 4,744,933; U.S. Pat. No. 5,132,117; and International Pub. WO 95/28227, all of which are incorporated herein by reference.

Liposomes can also be used to provide for the sustained release of the modified live Neospora cells of the invention, as long as at least some degree of viability of the modified live Neospora cells in the vaccine composition is maintained. Details concerning how to make and use liposomal formulations can be found in, among other places, U.S. Pat. No. 4,016,100; U.S. Pat. 4,452,747; U.S. Pat. No. 4,921,706; U.S. Pat. No. 4,927,637; U.S. Pat. No. 4,944,948; U.S. Pat. No. 5,008,050; and U.S. Pat. No. 5,009,956, all of which are incorporated herein by reference.

The present invention further provides a combination vaccine for protecting a mammal against neosporosis and, optionally, one or more other diseases or pathological conditions that can afflict the mammal, which combination vaccine comprises an immunologically effective amount of a first component comprising modified live Neospora cells; an immunologically effective amount of a second component capable of inducing a protective response against a disease or pathological condition that afflicts the mammal; and a veterinarily acceptable carrier.

The second component of the combination vaccine is selected based on its ability to induce a protective response against either neosporosis or another disease or pathological condition that can afflict members of the mammalian species, as known in the art. Any immunogenic composition known to be useful in a vaccine composition in the particular mammalian species can be used in the second component of the combination vaccine, as long as at least some degree of viability of the modified live Neospora cells in the resulting vaccine composition is maintained. Such immunogenic compositions include but are not limited to those that provide protection against pathogens selected from the group consisting of bovine herpes virus (syn., infectious bovine rhinotracheitis), bovine respiratory syncitial virus, bovine viral diarrhea virus, parainfluenza virus types I, II or III, Leptospira spp., Campylobacter spp., *Staphylococcus aureus, Streptococcus agalactiae*, Mycoplasma spp., Klebsiella spp., Salmonella spp., rotavirus, coronavirus, rabies, *Pasteurella hemolytica, Pasteurella multocida*, Clostridia spp., Tetanus toxoid, *E. coli*, Cryptosporidium spp., Eimeria spp., Trichomonas spp., and other eukaryotic parasites, among many others.

The combination vaccine of the present invention can further comprise one or more additional immunomodulatory components including, e.g., an adjuvant or cytokine, as described above, as long as the viability of the cells in the vaccine composition is maintained. The antigens of the combination vaccine can be stored in frozen form and thawed prior to administration.

The present invention further provides a method of protecting a mammal against neosporosis, comprising administering to the mammal a vaccine comprising an immunologically effective amount of modified live cells of Neospora of the present invention, and a veterinarily acceptable carrier. The vaccine is preferably administered parenterally, e.g., either by subcutaneous or intramuscular injection. However, the vaccine may instead be administered by intraperitoneal or intravenous injection, or by other routes, including, e.g., orally, intranasally, rectally, vaginally, intraocularly, or by a combination of routes, and also by delayed release devices as known in the art. The skilled artisan will know how to formulate the vaccine composition according to the route chosen.

An effective dosage can be determined by conventional means, starting with a low dose of modified live Neospora cells, and then increasing the dosage while monitoring the effects. Numerous factors can be taken into consideration when determining an optimal dose per animal. Primary among these is the species, size, age and general condition of the animal, the presence of other drugs in the animal, the virulence of a particular species or strain of Neospora against which the animal is being vaccinated, and the like. The actual dosage is preferably chosen after consideration of the results from other animal studies.

Vaccine regimens can also be selected based on the above-described factors. The vaccine of the invention can be administered at any time during the life of a particular animal depending upon several factors including, e.g., the timing of an outbreak of neosporosis among other animals, etc. The vaccine can be administered to animals of weaning age or younger, or to more mature animals, e.g., as a pre-breeding vaccine to protect against Neospora-related congenital disease or abortion. Effective protection may require only a primary vaccination, or one or more booster vaccinations may also be needed. One method of detecting whether adequate immune protection has been achieved is to determine seroconversion and antibody titer in the animal after vaccination. The timing of vaccination and the number of boosters, if any, will preferably be determined by a veterinarian based on analysis of all relevant factors, some of which are described above.

The amount of modified live Neospora cells in the vaccine preferably ranges from about $1\times10^3$ to about $1\times10^8$/ml, and more preferably from about $1\times10^5$ to about $1\times10^7$/ml. A suitable dosage size ranges from about 0.5 ml to about 10 ml, and more preferably from about 1 ml to about 5 ml.

The vaccine of the present invention is useful to protect mammals against neosporosis. As used herein, the term "mammal" refers to any mammalian species that can be protected against neosporosis using the vaccine of the invention, including dogs, cows, goats, sheep and horses, among others. The vaccine is useful to protect both pregnant and non-pregnant mammals.

The present invention further provides a kit for vaccinating a mammal against neosporosis, comprising a first container having an immunologically effective amount of modified live Neospora cells of the present invention. In a preferred embodiment, the present invention further comprises a second container having a veterinarily acceptable carrier or diluent. The modified live cells of the kit can be stored in frozen form and thawed prior to administration.

The following example is illustrative only, and is not intended to limit the scope of the present invention.

5. EXAMPLE

Isolation of the Neospara DHFR-TS Gene

5.1. Amplification Of Exon 1 Of DHFR Domain Of *N caninum*

Twenty-base long oligonucleotide primers specific to the 5' and 3' ends of the DNA sequence of exon 1 of the DHFR-TS gene of *T. gondii* were designed and synthesized, as based on the published sequence of the DHFR-TS gene of *T. gondii* (Roos, 1993, J. Biol. Chem. 268:6269–6280). *N. caninum* strain NC-1 genomic DNA was prepared using the GNOME™ kit (Bio 101, La Jolla, Calif.) using reagents and protocols provided by the manufacturer. PCR was carried out with 0.5 µg genomic DNA; 120 pmol each of primers Tgdhfrexon1-5' (5'-ATGCAGAAACCGGTGTGTCT) (SEQ ID NO:4) and Tgdhfrexon1-3' (5'-AGGGAAGAGGAAACGACGAT) (SEQ ID NO:5); 2.5 mM each of dATP, dGTP, dCTP, and dTTP (Perkin-Elmer, Norwalk, Conn.); PCR buffer (Perkin-Elmer); and 1.5 U AMPLITAQ™ DNA polymerase (Perkin-Elmer). The PCR cycle was 1 cycle of 94° C. for 1 min; and 29 cycles of 94° C. for 1 min, 55° C. for 1 min, 72° C. for 1 min.

A PCR product of about 0.3 kb was obtained and cloned into a pCRII vector (Invitrogen, Carlsbad, Calif.) without further treatment using T4 DNA ligase. The cloned ~0.3 kb fragment was sequenced by the dideoxy chain termination sequencing method, and the sequence was determined to be >85% homologous to the corresponding DHFR-TS exon 1 sequence of *T. gondii*.

5.2. Cloning And Sequencing Of The Neospora DHFR-TS Gene

A library of *N. caninum* strain NC-1 genomic DNA was made in bacteriophage vector λDASHII (Stratagene, La Jolla, Calif.). The ~0.3 kb fragment from above was radiolabelled with α-$^{32}$P-dCTP, and approximately $5\times10^5$ phage clones were screened for reactivity to the labelled fragment by plaque hybridization. Following three rounds of screening to enrich for reactive clones, 12 phage clones reactive to the ~0.3 kb sequence were identified.

Bacteriophage λ clone DNA was made from 3 of the 12 positive clones using a λ DNA isolation system (Qiagen, Chatsworth, Calif.) according to manufacturer's protocols. DNA from one of the λ phage clones, which clone has been designated as λNclDHFRTS (ATCC Accession No. 209512) (also designated as 4C13 or λCY50), was digested with NotI to release an 11 kb DNA fragment which was subcloned according to procedures described in Sambrook et al., 1989, above. PCR was conducted on DNA of a plasmid subclone containing the 11 kb DNA fragment using the following oligonucleotides, which were designed based on the DHFR-TS sequence: 5'-CCCCTCGTGGACCGGCTGAATA (SEQ ID NO:6); 5'-TCCGTG CGTGCCAAGAGACTG (SEQ ID NO:7); 5'-ATGGAGATGGCGATGGGAGGAC (SEQ ID NO:8); and 5'-AGTATGTACACGAAGCCTCMT (SEQ ID NO:9). Oliogonucleotides were used in PCR in the following combinations: SEQ ID NOS: 6 & 8; SEQ ID NOS: 6 & 9; SEQ ID NOS: 7 & 8; and SEQ ID NOS: 7 & 9. The PCR yielded specific products suggesting the presence of the Neospora DHFR-TS gene within the 11 kb fragment. Further restriction analysis of the 11 kb fragment-containing plasmid subclone indicated the presence of an asymmetric HindIII site within ~1.5 kb of one of the NotI sites. The DNA sequence was then determined from the NotI site at one end to the HindIII site at the other end (~9.6 kb) by primer walking applying the dideoxy chain termination sequencing method. DNA sequences thus obtained were analyzed using the computer software program DNASTARTM (DNASTAR Inc., Madison, WI).

The length of the above-sequenced fragment is 9603 bp (SEQ ID NO:1), and contains the sequence of the entire DHFR-TS gene from *N. caninum* strain NC-1. The nucleotide sequence of the Neospora DHFR-TS gene was compared to that of the published sequence of the DHFR-TS gene for *T. gondii* to predict locations of exons and introns, as well as the boundaries of the DHFR and TS domains. The Neospora DHFR-TS gene is predicted to contain 10 exons and 9 introns, as follows: Exon 1—from <2405–2724; Exon 2—from 3212–3348; Exon 3—from 3925–4262; Exon 4—from 4491–4737; Exon 5—from 5214–5307; from 5678–5750; Exon 7—from 6129–6270; Exon 8—from 6685–6777; Exon 9—from 7264and Exon 10—from 8116→8199. Consensus splice signals are present at the intron-exon junctions. The predicted DHFR domain is from about nt 2405 to about nt 4664; and the predicted TS domain is from about nt 4665 to about nt 8199, as based on structural analogy to the published *T. gondii* DHFR-TS sequence.

The predicted open reading frame (ORF) encoding the DHFR-TS protein from N. caninum strain NC-1 is 1,839 bp in length (SEQ ID NO:2). The ORF encoding the predicted DHFR domain is from about nt 1 to about nt 969. The ORF encoding the predicted TS domain is from about nt 970 to about nt 1836. The deduced amino acid sequence of the DHFR-TS protein of *N. caninum* strain NC-1 is 612 amino acids in length (SEQ ID NO:3). The deduced amino acid sequence comprising the predicted DHFR domain is from about amino acid residue 1 to about amino acid residue 323; the deduced amino acid sequence comprising the predicted TS domain is from about amino acid residue 324 to about amino acid residue 612. Sequence analysis indicates 73 amino acid differences in the DHFR domain and 15 amino acid differences in the TS domain between the deduced amino acid sequence of *N. caninum* and the predicted *T. gondii* DHFR-TS sequence.

Deposit Of Biological Material

The following biological material was deposited on Dec. 3, 1997 with the American Type Culture Collection (ATCC), which is currently at 10801 University Blvd., Manassas, Va. 20110–2209 USA, and was assigned the following accession number:

phage λNclDHFRTS ATCC Accession No. 209512.

All patents, patent applications, and publications cited above are incorporated herein by reference in their entirety.

The present invention is not limited in scope by the specific embodiments described, which are intended as single illustrations of individual aspects of the invention. Functionally equivalent compositions and methods are within the scope of the invention. Indeed, various modifications of the invention, in addition to those shown and described herein, will become apparent to those skilled in the art from the foregoing description. Such modifications are intended to fall within the scope of the appended claims.

What is claimed is:

1. An isolated polynucleotide molecule comprising a nucleotide sequence that encodes the amino acid sequence of SEQ ID NO:3 or the amino acid sequence encoded by the DHFR-TS gene present in phage λNclDHFRTS (ATCC Accession No. 209512).

2. The isolated polynucleotide molecule of claim 1, comprising the nucleotide sequence of SEQ ID NO:1 from nt 8199, or the nucleotide sequence of SEQ ID NO:2.

3. The isolated polynucleotide molecule of claim 1, comprising the nucleotide sequence of SEQ ID NO:1.

4. The isolated polynucleotide molecule of claim 1, comprising a nucleotide sequence that is a degenerate variant of: (i) the nucleotide sequence of SEQ ID NO:1 from nt. 2405 to nt 8199, or (ii) the nucleotide sequence of SEQ ID NO:2.

5. A recombinant vector comprising a polynucleotide molecule that encodes the amino acid sequence of SEQ ID NO:3 or the amino acid sequence encoded by the DHFR-TS gene present in phage λNclDHFRTS (ATCC Accession No. 209512).

6. The recombinant vector of claim 5, wherein the polynucleotide molecule comprises the nucleotide sequence of SEQ ID NO:1 from nt. 2405 to nt 8199, or the nucleotide sequence of SEQ ID NO:2.

7. A host cell comprising the recombinant vector of claim 5.

8. An isolated polynucleotide molecule comprising a nucleotide sequence that encodes amino acid residues 1 to 323 of: (i) the amino acid sequence of SEQ ID NO:3, or (ii) the amino acid sequence encoded by the DHFR-TS gene present in phage λNclDHFRTS (ATCC Accession No. 209512).

9. The isolated polynucleotide molecule of claim 8, comprising the nucleotide sequence of nt 2405 to nt 4664 of SEQ ID NO:1, or nt 1 to nt 969 of SEQ ID NO:2.

10. The isolated polynucleotide molecule of claim 8, comprising a degenerate variant of the nucleotide sequence of nt 2405 to nt 4664 of SEQ ID NO:1, or nt 1 to nt 969 of SEQ ID NO:2.

11. A recombinant vector comprising the polynucleotide molecule of claim 8.

12. A host cell comprising the recombinant vector of claim 11.

13. An isolated polynucleotide molecule comprising a nucleotide sequence that encodes the amino acid residues 324 to 612 of: (i) the amino acid sequence sequence of SEQ ID NO:3 or (ii) the amino acid sequence encoded by the DHFR-TS gene present in phage λNclDHFRTS (ATCC Accession No. 209512).

14. The isolated polynucleotide molecule of claim 13, comprising the nucleotide sequence of nt 4665 to nt 8199 of SEQ ID NO:1, or nt 970 to nt 1836 of SEQ ID NO:2.

15. The isolated polynucleotide molecule of claim 13, comprising a degenerate variant of the nucleotide sequence of nt 4655 to nt 8199 of SEQ ID NO:1, or nt 970 to nt 1836 of SEQ ID NO:2.

16. A recombinant vector comprising the polynucleotide molecule of claim 13.

17. A host cell comprising the recombinant vector of claim 16.

18. A method of preparing a DHFR-TS protein, comprising culturing a host cell transformed with a polynucleotide molecule comprising a nucleotide sequence that encodes the amino acid sequence of SEQ ID NO:3, or a cell clonally propagated therefrom, under conditions conductive to the expression of the DHFR-TS protein, and recovering the DHFR-TS protein from the cell culture.

* * * * *